(12) United States Patent
Hack et al.

(10) Patent No.: US 8,235,949 B2
(45) Date of Patent: Aug. 7, 2012

(54) APPLICATION SYSTEMS FOR USE WITH MEDICAL DEVICES

(75) Inventors: Dennis P. Hack, Cheswick, PA (US); Francis J. Sciulli, Jr., Crafton, PA (US); Charles J. Mutschler, Wexford, PA (US); R. Reade Harpham, Columbus, OH (US); Daniel A. Kramer, Dublin, OH (US); Felicia R. Ruggeri, Grandview Heights, OH (US); Jan B. Yates, Reynoldsburg, OH (US); William G. Atterbury, Columbus, OH (US); Joseph A. Juratovac, Columbus, OH (US); Jeffery R. Held, Columbus, OH (US); Chad E. Bouton, Delaware, OH (US); James B. Gleeson, Columbus, OH (US)

(73) Assignee: Medrad, Inc., Indianola, PA (US)

( * ) Notice: Subject to any disclaimer, the term of this patent is extended or adjusted under 35 U.S.C. 154(b) by 1480 days.

(21) Appl. No.: 11/223,792

(22) Filed: Sep. 9, 2005

(65) Prior Publication Data
US 2006/0135884 A1    Jun. 22, 2006

Related U.S. Application Data

(60) Provisional application No. 60/609,100, filed on Sep. 10, 2004.

(51) Int. Cl.
*A61M 5/32* (2006.01)
*A61B 5/05* (2006.01)
(52) U.S. Cl. ........................................ 604/180; 600/547
(58) Field of Classification Search .................. 600/382; 606/75
See application file for complete search history.

(56) References Cited

U.S. PATENT DOCUMENTS

| | | | |
|---|---|---|---|
| 4,647,281 A | 3/1987 | Carr | |
| 4,877,034 A | 10/1989 | Atkins et al. | |
| 5,334,141 A | 8/1994 | Carr et al. | |
| 5,947,910 A | 9/1999 | Zimmet | |
| 5,954,668 A | 9/1999 | Uber, III et al. | |
| 5,964,703 A | 10/1999 | Goodman et al. | |
| 6,408,204 B1 * | 6/2002 | Hirschman | 600/547 |
| 2006/0135884 A1 | 6/2006 | Hack et al. | |
| 2006/0211970 A1 | 9/2006 | Sciulli | |

FOREIGN PATENT DOCUMENTS

| | | |
|---|---|---|
| WO | 03009752 | 2/2003 |
| WO | 03009753 | 2/2003 |

* cited by examiner

*Primary Examiner* — Nicholas Lucchesi
*Assistant Examiner* — Pritesh Patel
(74) *Attorney, Agent, or Firm* — Jill Denesvich

(57) ABSTRACT

An application or an attachment device for attaching a medical device includes a base layer and an adhesive layer on a rearward side of the base layer. The adhesive layer is adapted to removably attach the base layer. The adhesive layer can be adapted to removably attach the base layer to a patient (either a human patient or a lower animal patient). The device also includes a medical device attachment mechanism on a forward side of the base layer. The attachment mechanism is adapted to attach the medical device to the base layer. The medical device can, for example, be a sensor. The medical device attachment mechanism can, for example, include a mechanical attachment mechanism. The medical device attachment mechanism can additionally or alternatively include at least one adhesive layer on the base layer. The adhesive layer can, for example, be positioned on the base layer so that it does not extend beyond a footprint of the medical device when the medical device is attached to the base layer.

24 Claims, 14 Drawing Sheets

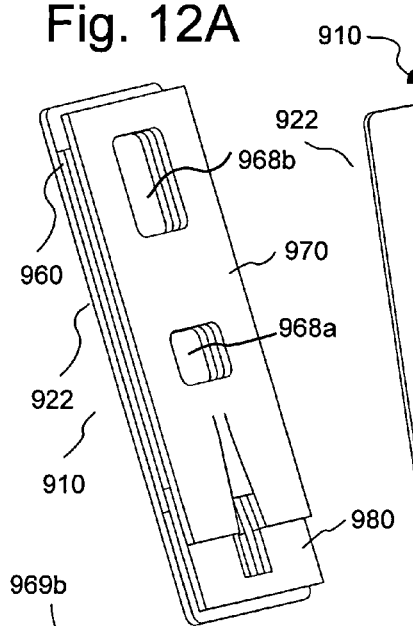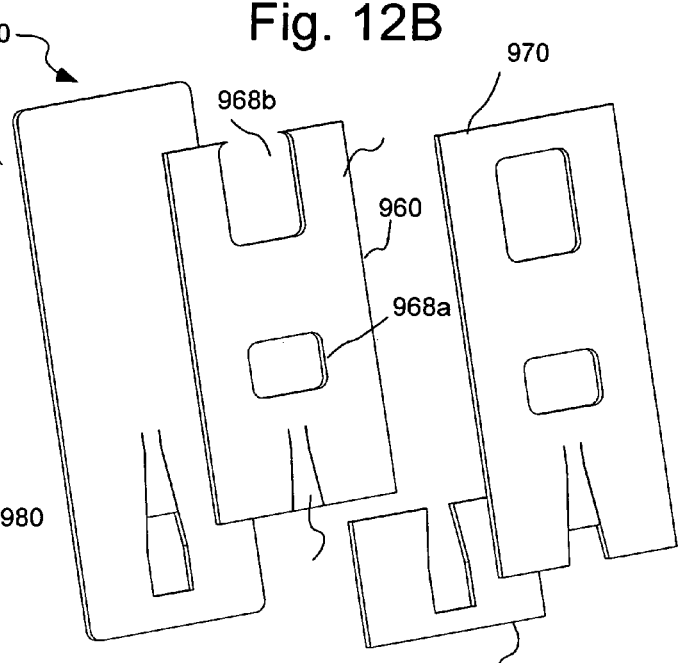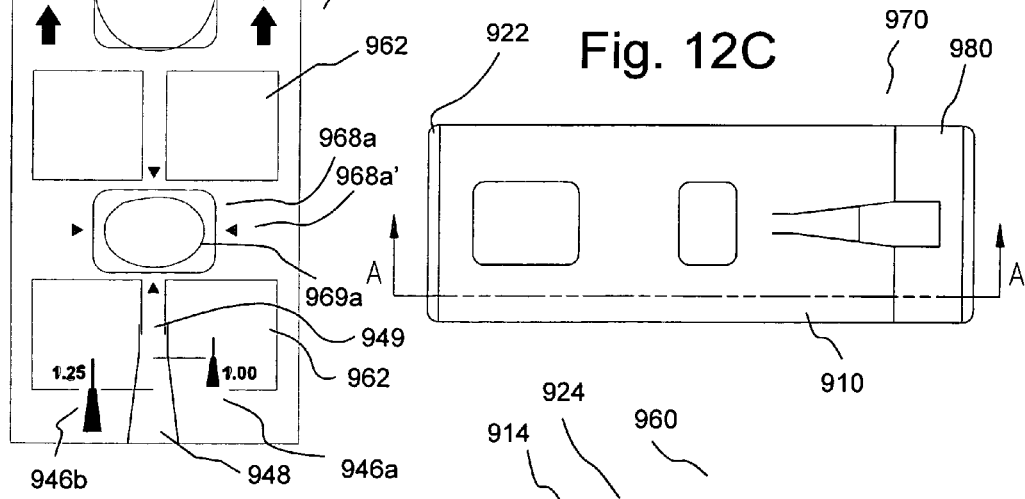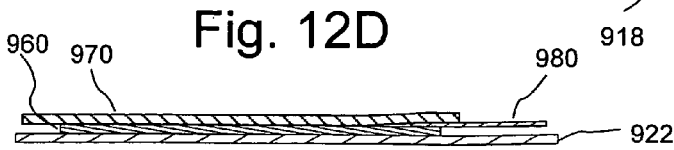

APPLICATION SYSTEMS FOR USE WITH MEDICAL DEVICES

CROSS-REFERENCE TO RELATED APPLICATION

This application claims the benefit of U.S. Provisional Patent Application Ser. No. 60/609,100, filed Sep. 10, 2004, the disclosure of which is incorporated herein by reference.

BACKGROUND OF THE INVENTION

The present invention relates generally to application devices, systems and methods for use with medical devices and, particularly, to application or attachment devices, systems and methods for use in the medical field to releasably attach a medical device such as a sensor to a patient (either a human patient or a so called lower animal patient).

Adhesive sheets or adhesive materials such as adhesive tapes are widely used in the medical field. For example, adhesive tapes are used to maintain certain medical devices (for example, catheters, sensors etc.) in close proximity to the body of a patient.

One type of sensor that can be adhered to patient is an extravasation sensor. Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modern procedures can increase the risk of extravasation. In computed tomography, for example, contrast injection flow rates can be in the range of 0.1 to 10 ml/s. Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection site resulting from extravasation. By visual observation, it is also sometimes possible to observe directly any swelling of the skin in the vicinity of an injection site resulting from extravasation.

In addition to palpation and observation, there are a number of automated or sensor-base methods of detecting extravasation that may include automatic triggering of an alarm condition upon detection. Sensor configurations that also provide an area for palpation and/or observation are discussed, for example, in U.S. Pat. No. 6,408,204, assigned to the assignee of the present invention, the disclosure of which is incorporated herein by reference.

Several plethysmographic extravasation detection techniques and sensors are available. For example, mercury strain gauge plethysmographs measure the volume change resulting from venous blood flow in a cross sectional area of a limb of a patient. Air cuff or pulse volume recorder plethysmographs measure the changes in pressure within a recording cuff.

Impedance plethysmographs use low-frequency electromagnetic energy transmitted via galvanic contact with the skin to measure changes in the electrical impedance in a defined tissue volume of a limb. Detection of extravasation via impedance changes is disclosed, for example, in U.S. Pat. Nos. 5,964,703 and 5,947,910.

Photo-plethysmographs measure the optical scattering properties of capillary blood to detect the presence of extravasated fluids in tissue. An example of a photo-plethysmograph is described in U.S. Pat. No. 4,877,034.

A number of extravasation detection devices attempt to measure temperature differences to determine if an extravasation has occurred. For example, U.S. Pat. No. 4,647,281 discloses subcutaneous temperature sensing of extravasation to trigger an alarm. U.S. Pat. No. 5,954,668 also discloses use of a microwave antenna to sense temperature of tissue to detect extravasation.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween. The sensor detect changes from normal microwave emissions from a patient that result from extravasation.

Published PCT International Application Nos. WO 03/009753 and WO 03/009752, assigned to the assignee of the present invention, the disclosures of which are incorporated herein by reference, disclose sensors that use electromagnetic energy such as microwave energy to sense changes in permittivity of tissue to sense buildup of fluids within the tissue to determine, for example, if extravasation or edema is present. The sensors include at least one electromagnetic energy transmitter for directing energy into a volume of tissue and at least one electromagnetic energy receiver to measure a resultant signal.

In many instances in which a medical device such as an extravasation sensor must be held in contact with a patient, adhesive tape is simply pulled over a device and adhered to the patient to maintain the device in connection with the patient. Likewise, many bandages or other tissue coverings include an adhesive material. Often it is difficult to remove such adhesive tapes, strips or sheets from connection with the patient. Moreover, removal of such adhesive materials from the patient is often a painful experience for the patient. U.S. patent application Ser. No. 11/082,209, entitled RELEASABLE APPLICATION SYSTEMS AND RELEASABLE MEDICAL DEVICE SYSTEMS, filed Mar. 16, 2005, assigned to the assignee of the present invention, the disclosure of which is incorporate herein by reference, discloses the use of releasable adhesive devices to attach various sensors to a patient and to provide a tissue covering after a sensor is removed.

Although some advances have been made in the attachment of medical devices, including sensors, to patients, a number of problems persist. For example, in a number of such devices such as the sensors disclosed in Published PCT International Application Nos. WO 03/009753 and WO 03/009752, a number of factors including, but not limited to, the nature of the contact (direct or indirect) of the sensor with the patient's tissue (for example, skin) and the position and/or orientation of the sensor(s) with respect to the patient and other medical devices can be important to the operation of the sensor. Moreover, many sensors and other medical devices have a number of operating components that are preferably attached to the patient or otherwise stabilized for proper operation and/or stabilization. Typically, attachment of such components requires the use of multiple strips of adhesive tape, which may not be readily available to medical personnel or may be cumbersome to obtain and apply. Moreover, such strips are typically not sterile and their use does not follow good aseptic technique.

It thus remains desirable to develop devices, systems and methods whereby a medical device can be releasably or removably attached to a patient.

SUMMARY OF THE INVENTION

In one aspect, the present invention provides an application or an attachment device for attaching a medical device. The device includes a base layer and an adhesive layer on a rearward side of the base layer. The adhesive layer is adapted to removably attach the base layer. The adhesive layer can be adapted to removably attach the base layer to a patient (either a human patient or a lower animal patient). The device also includes a medical device attachment mechanism on a forward side of the base layer, The attachment mechanism is adapted to attach the medical device to the base layer. The medical device can, for example, be a sensor. The medical device attachment mechanism can, for example, include a mechanical attachment mechanism. The medical device attachment mechanism can additionally or alternatively include at least one adhesive layer on the base layer. The adhesive layer can, for example, be positioned on the base layer so that it does not extend beyond a footprint of the medical device when the medical device is attached to the base layer.

In one embodiment, the medical device is an extravasation sensor for use in an procedure in which a fluid path is used to transport a fluid into a patient. In this and other embodiments, the base layer can include at least one open area to, for example, enable at least one of palpation or visualization of an area of the patient. In several embodiments, two open areas are provided. A first open area can, for example, be positioned to encompass an end of a catheter needle when the device is attached to a patient. A second open area can, for example, be positioned to be toward the heart of the patient relative to the first open area when the device is attached to a patient. A transparent, flexible material can cover one or more of such open areas to, for example, assist in preventing contamination.

The device can further include at least one application guide to position the device at a desired position on the patient. Likewise, the device can further include at least one medical device guide to position the medical device at a desired position on the device. In the case of, for example, an extravasation sensor for use in an procedure in which a catheter is used to transport a fluid into a patient, the application guide can assist in positioning the device relative to the catheter. The application guide can, for example, include an indicator on the base layer of the device.

The device can further include at least one adhesive strip removably attached to the base layer. The adhesive strip has an adhesive on a rearward side thereof. The adhesive strip can, for example, include an indicator or indicators thereon representative of a proposed use thereof or representative of a recommended or proposed order of use thereof. A plurality of adhesive strip can be removably attached to the base layer.

The device can further include a section adapted to cover at least a portion of a catheter when the device is attached to a patient. The section can, for example, cover an area in which a catheter enters (or punctures the skin of) the patient when the device is attached to a patient.

In other aspects, the present invention provides methods of attachment of medical devices using a device as described above.

In another aspect, the present invention provides a device for dispensing adhesive strips in a medical setting. The adhesive strip dispensing device includes a backing layer; and a plurality of adhesive strips removably adhered to a forward side of the backing layer. Each of the adhesive strips includes a base layer and an adhesive layer on the rearward side of the base layer. The adhesive layer removably adheres the adhesive strip to the backing layer. At least a portion of the adhesive layer remains in contact with the base layer after removal of the adhesive strip from the backing layer. The remaining adhesive layer is suitable to adhere the adhesive strip to, for example, an object and/or a patient. The dispensing device can be fabricated from sterilizable materials. Each of the plurality of adhesive strips can include a tab connected to the base layer that can be grasped by a user to remove each of the adhesive strips from the backing layer. The dispensing device can further include a layer of adhesive over at least a portion of a rearward side of the backing layer to enable removable attachment of the dispensing device to an article to enable ready access to the adhesive strips. Such attachment to an article (for example, a table) frees a practitioner's hands to use in other tasks and thereby decreases procedure time. As compared to current practices in dispensing adhesive tape (typically, cut to size from a roll of adhesive tape), the adhesive strip dispensing devices of the present invention decrease time, decrease steps, and generally decrease operator frustration, particularly when such operators perform multiple (for example, 25 or more) of the same procedures in a single day.

The backing layer can, for example, have a stiffness greater than each of the plurality of adhesive strips to, for example, facilitate removal of such adhesive strips. The adhesive strips can, for example, be fabricated of materials having sufficient thickness and tensile modulus to resist curling when subjected to the peel force required to remove each of the plurality of adhesive strips from the backing layer.

In other aspects, the present invention provides methods of providing adhesive tape strips including the step of providing a dispensing device as described above. Such methods are quite useful in the medical arts, and particularly useful in repetitive medical procedures in which similar adhesive strips (for example, similar in size, shape, peel strength etc.) are required repeatedly between procedures.

In a further aspect, the present invention provides a system for attaching a medical device, including a medical device attachment device and a device for dispensing adhesive strips. As described above, the medical device attachment device includes a base layer and an adhesive layer on a rearward side of the base layer. The adhesive layer is adapted to removably attach the base layer. The medical device attachment device further includes a medical device attachment mechanism on a forward side of the base layer. The attachment mechanism is adapted to attach the medical device to the base layer. The device for dispensing adhesive strips includes a backing layer and a plurality of adhesive strips removably adhered to a forward side of the backing layer. Each of the adhesive strips includes a base layer and an adhesive layer on the rearward side of the base layer. The adhesive layer removably adheres the adhesive strip to the backing layer. At least a portion of the adhesive layer remains in contact with the base layer after removal of the adhesive strip from the backing layer.

In another aspect, the present invention provides a system for detection of extravasation including a sensor having at least one transmitting antenna to apply electromagnetic energy in the frequency range of approximately 300 MHz to approximately 30 GHz a first volume of the body over a period of time and at least one receiving antenna to measure a resultant signal. The system also includes a device for attaching the sensor to a patient. The attachment device includes a base layer and an adhesive layer on a rearward side of the base layer. The adhesive layer is adapted to removably attach the base layer. The attachment device further includes a sensor attachment mechanism on a forward side of the base layer. The sensor attachment mechanism is adapted to removably attach the sensor to the base layer.

The sensor attachment mechanism can, for example, include at least one adhesive layer on the base layer. The adhesive layer can be positioned on the base layer so that it does not extend beyond a footprint of the sensor when the sensor is attached to the base layer.

The base layer of the sensor attachment device can include at least one open area to enable at least one of palpation or visualization of an area of the patient. The sensor attachment device can further include at least one application guide to position the sensor attachment device at a desired position on the patient. The sensor attachment device can include at least one sensor guide to position the sensor at a desired position on the sensor attachment device. The application guide can, for example, assist in positioning the sensor attachment device relative to a catheter. The application guide can include at least one indicator on the base layer of the device.

The sensor attachment device can further include at least one adhesive strip removably attached to the base layer. The adhesive strip has an adhesive on a rearward side thereof. The adhesive strip can include an indicator or indicators thereon representative of a proposed use thereof and/or representative of a recommended order of user thereof relative to another section of the sensor attachment device.

The system can include a device for dispensing adhesive strips as described above.

In another aspect, the present invention provides a device for attaching a medical device including a base layer. The base layer is divided into a plurality of base layer sections. A adhesive layer is provided on a rearward side of each of the base layer sections. The adhesive layer is adapted to removably attach each of the base layer sections. The device also includes a medical device attachment mechanism on a forward side of one of the base layer sections. The attachment mechanism is adapted to attach the medical device to one of the base layer sections. The base layer sections can be detachable from each other for separate application. One or more of the base layer sections can also remain connected during and or after application thereof. At least one of the base layer sections can include an indicator providing information such as a recommended use of the base layer section. At least one of the base layer sections can include an indicator providing information as to a recommended order of use of the base layer section relative to at least one other base layer section.

In still a further aspect, the present invention provides a device for attaching a medical device including a base layer suitable to reduce passage of contaminants between patient and the medical device. The device also includes an adhesive layer on a rearward side of the base layer. The adhesive layer is adapted to removably attach the base layer to a patient. The device further includes a medical device attachment mechanism on a forward side of the base layer. The attachment mechanism is adapted to attach the medical device to the base layer. The adhesive layer of this device and other devices of the present invention can include a bioactive agent.

BRIEF DESCRIPTION OF THE DRAWINGS

Other aspects of the invention and their advantages will be discerned from the following detailed description when read in connection with the accompanying drawings, in which:

FIG. 12A illustrates a perspective view of another embodiment of an applicator or attachment device of the present invention for use with a sensor.

FIG. 12B illustrates a perspective, exploded or disassembled view of the applicator or attachment device of FIG. 12A.

FIG. 12C illustrates a top plan view of the applicator or attachment device of FIG. 12A.

FIG. 12D illustrates a cross-sectional view of the applicator or attachment device of FIG. 12A (section A-A, with reference to FIG. 12C).

FIG. 12E illustrated an expanded cross-sectional view of the sensor application portion of the applicator or attachment device of FIG. 12A.

FIG. 12F illustrates a top plan view of the sensor application portion of FIG. 12A with alignment indicia thereon.

DETAILED DESCRIPTION OF THE INVENTION

Figure 1:
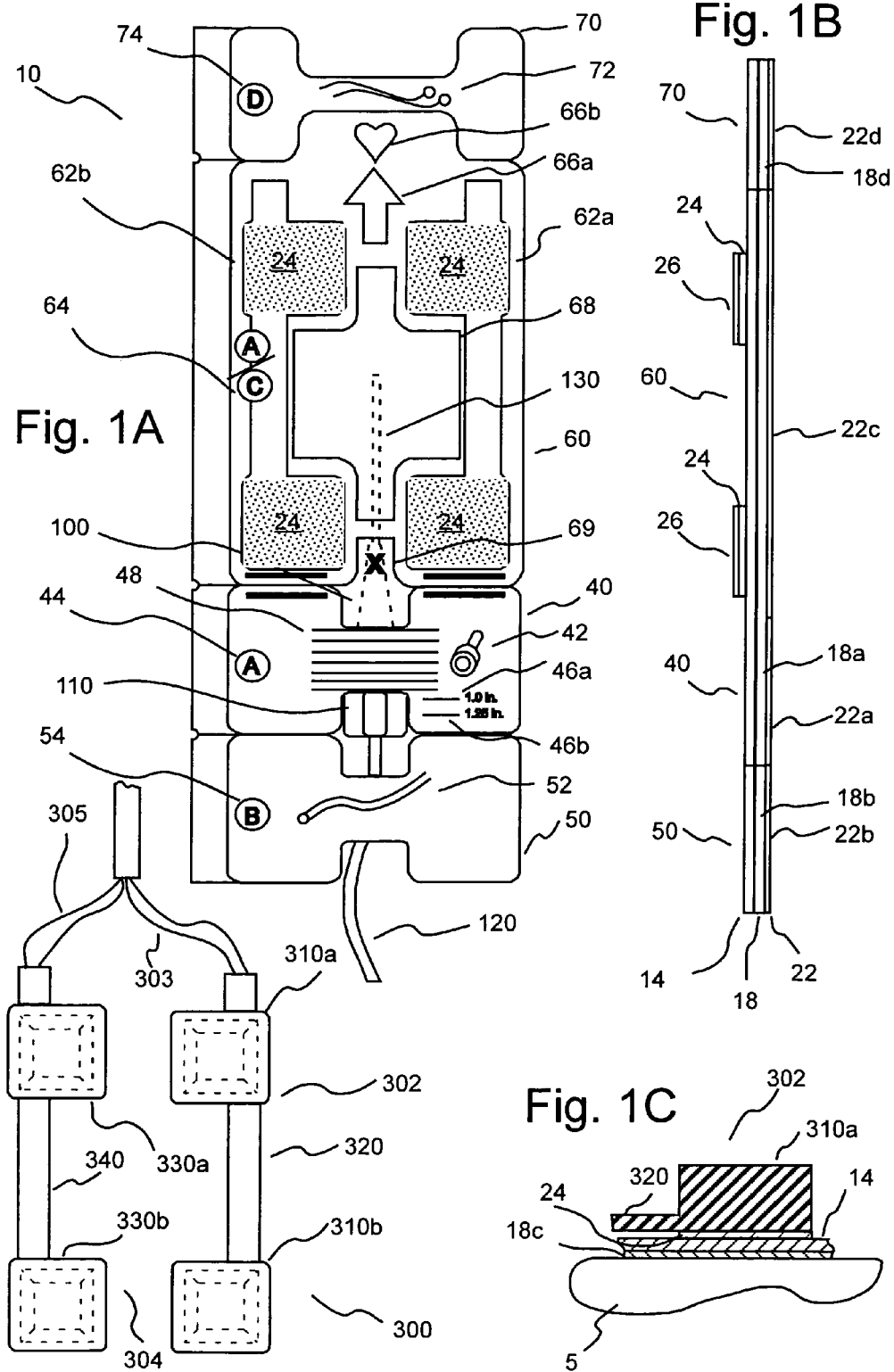
FIG. 1A illustrates a top plan view of an embodiment of a sensor system of the present invention including a sensor and an applicator or attachment device for use in removably attaching the sensor to a patient, wherein the sensor is not attached to the attachment device.
FIG. 1B illustrates a side cutaway view of the attachment device of FIG. 1A.
FIG. 1C illustrates a side cross-sectional view of a portion of the sensor and the attachment device of FIG. 1A wherein the sensor is attached to the attachment device and the attachment device is attached to a patient's arm.

FIGS. 1A through 1C illustrate an embodiment of a system of the present invention including an application or attachment device 10 of the present invention for use with a medical device such a extravasation sensor 300 as described in Published PCT International Application Nos. WO 03/009753 and WO 03/009752. Extravasation sensor 300 can, for example, include a transmitting unit 302 including two transmitting antennae 310a and 310b which are attached via a bridging member 320. Bridging member 320 can, for example, appropriately space transmitting antennae 310a and 310b with respect to each other and provide a conduit, pathway or support for electrical connection of transmitting antenna 310b to a controller (not shown in FIGS. 1A through 1C). Extravasation sensor 300 can further include a receiving unit 304 including two receiving antennae 330a and 330b which are attached via a bridging member 340, which can operate in a manner similar to bridging member 320. Sensor 300 can, for example, operate by applying electromagnetic energy (for example, in the frequency range of approximately 300 MHz to approximately 30 GHz) via transmitting antennae 310a and 310b of transmitting unit 302 to a volume of the body between transmitting unit 302 and receiving unit 304 and measuring a resultant or returned signal received by receiving antennae 330a and 330b of receiving unit 304. The measured signal can, for example, be compared to a reference signal to determine if the fluid level in the tissue has changed in a manner associated with an extravasation event. It is apparent to one skilled in the art that various other medical devices, including other sensor configurations are suitable for use with the attachment devices of the present invention.

As illustrated, for example, in FIGS. 1A and 1B, attachment device or applicator 10 can include a base layer 14 upon which various templates, guides and/or informational elements are positioned (for example, by printing thereof on base layer 14). As illustrated, for example, in FIG. 1B, on a first, rearward or lower major surface of base layer 14, an adhesive layer 18 can cover a portion or all of base layer 14. Adhesive layer 18 is suitable to attach application device 10 to a patient (for example, to a patient's skin). A cover or protective layer 22 can be attached to adhesive layer 18 on a side thereof opposite base layer 14 to protect adhesive layer 14 until device 10 or parts thereof are to be attached to a patient.

Device 10 is divided into several connected sections. A first section or catheter attachment section 40 is adapted (for example, appropriately dimensioned etc.) to cooperate with the hub 110 of a catheter 100 to hold catheter 100 in place in operative connection with the patient's skin. First section 10 can, for example, include a symbol 42 of a catheter hub to indicate the use thereof. First section 40 can also include an indicator 44 to inform an operator of a recommended relative order of attachment or use of first section 40 with respect to the other sections of device 10. In the case of attachment device 10, first section 40 is preferably used to attached catheter hub 100 to the patient before the other sections of device 10 are used. First section 40 thus includes an indicator such as an "A" or a "1". As clear to one skilled in the art, the order of use or attachment of the various sections of device 10 can be altered.

Prior to application, the user or operator can detach first section 40 from the remainder of device 10 or section 40 can be attached to catheter hub 110 and to the patient while it remains in contact with one other section of, more than one other section of or the entirety of device 10. The user must first remove at least a first section 22a of protective layer 22 from connection with a first section 18a of adhesive layer 18 over the area of first section 40 to expose first section 18a adhesive layer 18. Removal of first cover section 22a can be accomplished while allowing the remainder of cover section 22 to remain in contact with adhesive layer 18. Device 10 can, for example, be die stamped to create separations between the sections thereof. Likewise, perforations can be formed along section separations of cover layer 22 (and other layers of device 10) to facilitate removal of cover layer 22 (and other layers of device 10) in sections. Cover section 22 can also be removed as a whole and all the sections of device 10 attached to the patient simultaneously.

First section 40 also includes positioning indicators 46a and 46b that assist in properly positioning one or more sections of attachment device 10 with respect to catheter 100. In that regard, properly positioning third section or sensor section 60 of attachment device 10 with respect to catheter 100 results in proper or preferred positioning of sensor 300 with respect to catheter 100 and can result in improved measurements by sensor 300. Third section 60, which can remain in connection with first section 40 during attachment of those sections, is discussed further below. In the embodiment of FIGS. 1A through 1C, first section 40 includes two indicator designations 46a and 46b to properly or desirably position first section 40 with respect to a catheter needle 130 having a standard length 1.25 in. or a catheter needle 130 having a standard lengths and 1.0 in., respectively. As clear to one skilled in the art, additional and/or alternative indicators can be provided for catheter needles of other lengths. First section 40 can also include slits 48 formed therein to assist in conforming first section 40 to the shape of catheter hub 110.

After attachment of first section 40 to catheter 100 and to the patient, a tubing section or second section 50 of attachment device 10 can be attached to tubing 120 (which transports fluid to catheter 100) and to the patient. Second section 50 can operate to assist in maintaining catheter 100 in place, keep tubing 120 in a desired position relative to the patient and to relieve stress in tubing 120. Before application of second section 50, protective layer section 22b is first removed to expose adhesive layer section 18b. Second section 50 can include a symbol 52 of a tubing section to indicate the use thereof. Second section 50 can also include an indicator 44 to inform an operator of the relative order of attachment, application or use of second section 50 with respect to the other sections of device 10. In the case of attachment device 10, second section 50 is preferably removed from connection with first section 40 prior to application of first section 40 and used to attach tubing 120 to the patient after first section 40 of device 10 is applied to catheter 100. Second section 50 thus includes an indicator such as a "B" or a "2".

Third section or sensor section 60 can, for example, be attached after second section 50. Preferably, third section 60 is positioned on the patient adjacent first section 40 as illustrated in FIG. 1A to assist in properly positioning third section 60 to properly position third section 60 (and, subsequently, sensor 300) with respect to catheter needle 130. As described above, first section 40 and third section 60 can be applied or attached simultaneously in a connected state to accomplish this result. In that regard, as illustrated in FIG. 1B, in one embodiment third section 60 includes a third section 22c of protective layer which can be removed separately from first protective layer section 22a, but first section 40 and third section 60 include an integral adhesive layer 18a and an integral base layer. In this embodiment, second section 50 and fourth section 70 (discussed further below) can first be separated from device 10. First section 40 is then applied to catheter 100 as described above. During application of first section 40, third protective layer section 22c remains in connection with third section 60. After application of first section 40 (and possibly after subsequent attachment of second section 50), third section 60 can be folded upward relative to first section 40 and third protective layer section 22c removed to expose adhesive layer section 18a in the area of third section 60. Third section 60 is then applied to arm 5 (see FIG. 1C), taking care to avoid wrinkles and air pockets.

Third section 60 can include one or more guides, templates or alignment elements 62a and 62b that provide guidance to the user of how to attach sensor 300 to third section 60. In that regard, after attachment of third section 60 to the patient, a user simply places transmitting unit 302 within the bounds or guides of guiding element 62a and receiving unit 304 within the bounds or guides of guiding element 62b. Transmitting antennae 310a and 320b and receiving antennae 330a and 330b of sensor 300 can be made to have somewhat directional transmission and reception, respectively. It can thus be important that the antennae be oriented properly with respect to each other and with respect to the catheter needle. Proper use of guide elements 62a and 62b ensure proper position and orientation. Bridge members 320 and 340 operate to properly space transmitting antennae 310a and 310b and receiving antennae 330 and 330b, respectively, in a longitudinal or up and down direction. Guide elements 62a and 62b can operate to properly space transmitting unit 302 and receiving unit 304, respectively, in a latitudinal, lateral or side-to-side direction. Guide elements 62a and 62b can include adhesive layers 24 which are generally coextensive with the area of contact of antennae 310a, 310b, 330a and 330b with base layer 14 to removably connect antennae 310a, 310b, 330a and 330b to base layer 14 of third section 60. Cover layers 26 (see FIG. 1B) can be placed over adhesive layers 24 to protect adhesive layers 24 until use thereof.

Third section 60 further include one or more indicators such as arrow 66a and heart 66b that provide an indication of the direction in which device 10 should be applied to the body (for example, to a patient's arm). Arrow 66a and heart 66b indicate the direction in which device 10 should be place with direction of blood flow back to the heart. In that regard, the upper end of third section 60 (including arrow 66a and heart 66b) should be placed higher up on the arm of the patient, while the opposite or lower end of third section 60 should be placed lower on the arm.

Third section 60 also includes at least one "open" area 68 to enable visualization and/or palpation of the injection site as described, for example, in U.S. Pat. No. 6,408,204. Preferably, no adhesive is present in area 68. Area 68 can, for example, include an area of flexible, transparent polymeric material through which an operator can visualize and palpate the injection site. Preferably, no adhesive is present on the surface of area 68 to be palpated or on the rearward surface thereof. Area 68 can also be a cutaway section formed in third section 60 through which the operator can directly visualize and/or palpate the injection site. Third section 60 can further include a notch or opening 69 in the area of the site where catheter 100 punctures the skin of the patient (marked with an "x" in FIG. 1A) to facilitate positioning of third section 60 adjacent catheter 100.

As with the other sections of device 10, third section 60 can includes an indicator such as an "C" or a "3" to indicate the recommended or possible order of its use or application. An indicator such as "A/C" can be provided to indicate the use or application of third section 60 in connection with first section 40 as described above.

Device 40 further includes at least a fourth section 70 that can be used to attach cable leads 303 and 305 to, for example, the patient. Fourth section 70 includes a fourth protective layer section 22d, which is removed to expose a fourth adhesive layer section 18d prior to application of fourth section 70. Fourth section 70 also includes an indicator 72 representing cable leads to indicate the user thereof. Fourth section 70 further includes an indicator such as a "D" or a "4" to indicate a recommended or possible order of use thereof with respect to the other sections of device 10. In the case of certain sensors, precaution should be taken to prevent contact between and/or excessive motion of the cable leads. As set forth in Published PCT International Application Nos. WO 03/009753 and WO 03/009752, for example, such precautions may decrease motion artifact with the extravasations sensors thereof.

FIG. 1C illustrates a portion of attachment device 10 in operative connection with the skin of a patient's arm 5. Base layer 14 and adhesive layers 18 and 24 preferably ensure good operative connection or coupling between sensors 310a, 310b, 330a and 330b and the patient's skin. In that regard, wrinkles in base layer 14 should be avoided, Moreover, air pockets between the sensors and base layer 14 as well as between base layer 14 and the patients skin should be avoided. Air pockets can, for example, scatter energy, negatively affect coupling of the sensors with the skin and can cause increased artifacts as a result of subject/patient motion.

Materials used in device 10 are thus preferably chosen to prevent wrinkling upon application to the patient. As such materials contact the skin of the patient, they should be suitably biocompatible and not cause adverse reaction(s). The materials should not attenuate or scatter the energy applied to the patient's skin via sensor 300. Preferably, device 10 is made as thin as possible to avoid redirection of energy laterally. Adhesive layers 18 and 24 should provide suitable bond strength to maintain sensor 300 in connection with the patient during normal use of device 10, including during normal patient movement and during clinical interaction (for example, palpation). Base layer 14 should likewise be of sufficient strength to remain intact during normal use of device 10. The adhesive materials used in adhesive tape nos. 1513 and 1522 available from 3M of Saint Paul, Minn. are examples of adhesives suitable for use in the present invention. An example of a suitable material for base layer 14 is a polyester.

Figure 2:
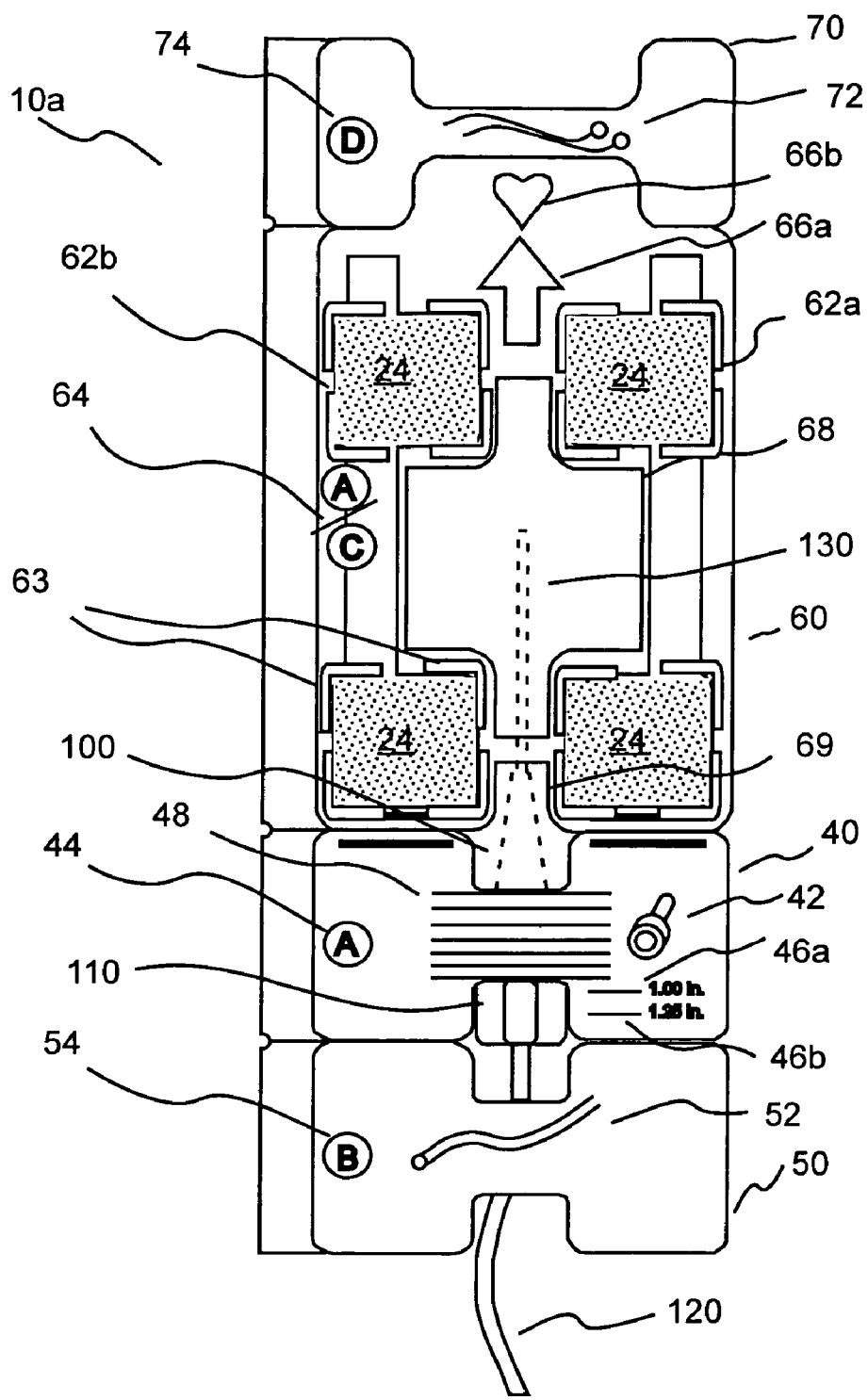
FIG. 2 illustrates a top plan view of another embodiment of an applicator or attachment device of the present invention including mechanical guides or attachment elements for attachment of a sensor as illustrated in FIG. 1A thereto.

FIG. 2 illustrates a device 10a including most of the same components of device 10, and such like components are numbered the same as in FIGS. 1A through 1C. In the embodiment of FIG. 2, device 10a further includes mechanical guides 63 in addition to printed guides 62a and 62b. Mechanical guides 63 can, for example, contact and form a snap fit with each of antennae 310a, 310b, 330a and 330b. Adhesive layers 24 can be eliminated if mechanical guides or connectors 63 form a suitable removable connection between antennae 310a, 310b, 330a and 330b and device 10.

Figure 3A:
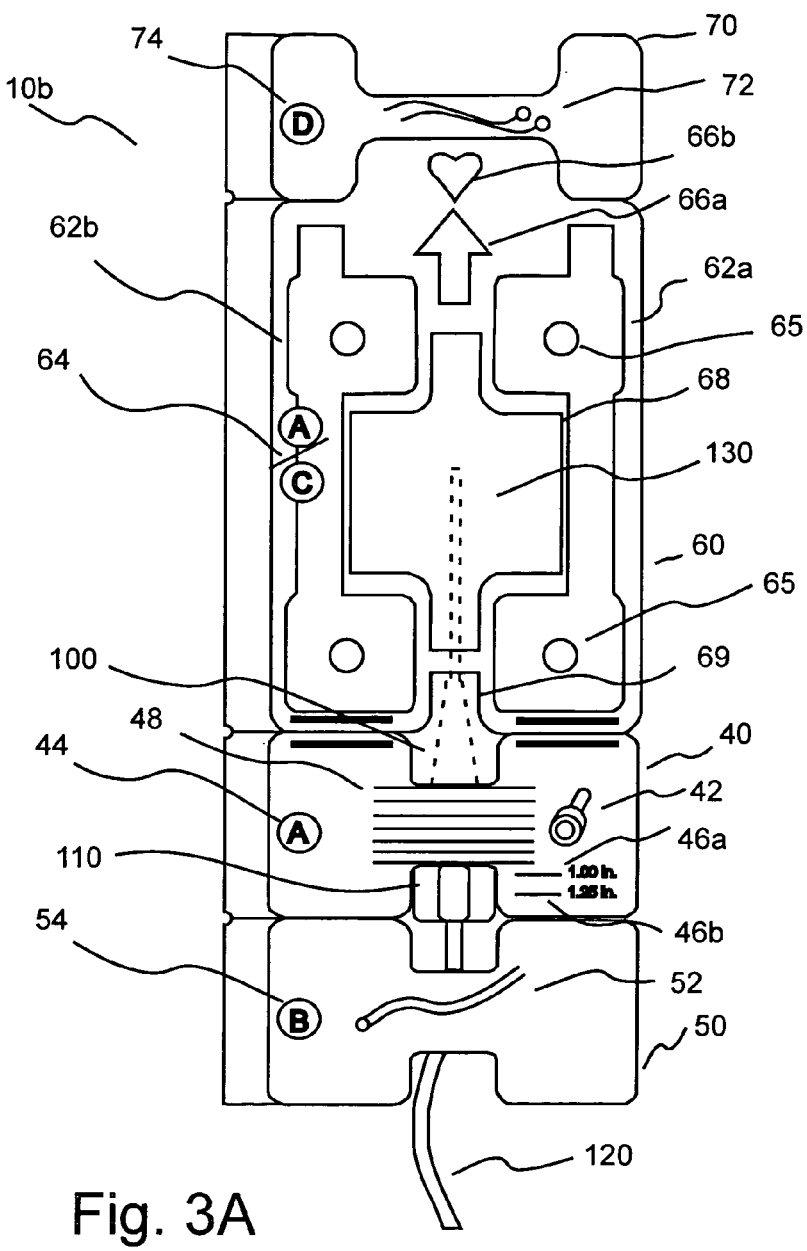
FIG. 3A illustrates a top plan view of another embodiment of an applicator or attachment device of the present invention including mechanical attachment elements for attachment of a sensor thereto.
Figure 3B:
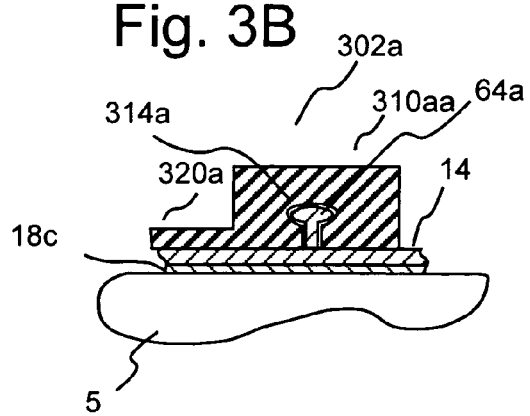
FIG. 3B illustrates a side cross-sectional view of a portion of the attachment device of FIG. 3A wherein a sensor is attached to the attachment device and the attachment device is attached to a patient's arm.

FIGS. 3A and 3B illustrate a device 10*b* including most of the same components of device 10, and like such components are numbered the same as in FIGS. 1A through 1C. In the embodiment of FIGS. 3A and 3B device 10*b* includes mechanical attachment elements 65. Mechanical attachment elements 65 form a snap fit with recesses 314*a* formed in, for example, a sensor antennae 310*aa* as illustrated in FIG. 3B. Adhesive layers 24 are absent in the embodiment of FIGS. 3A and 3B.

Figure 4:
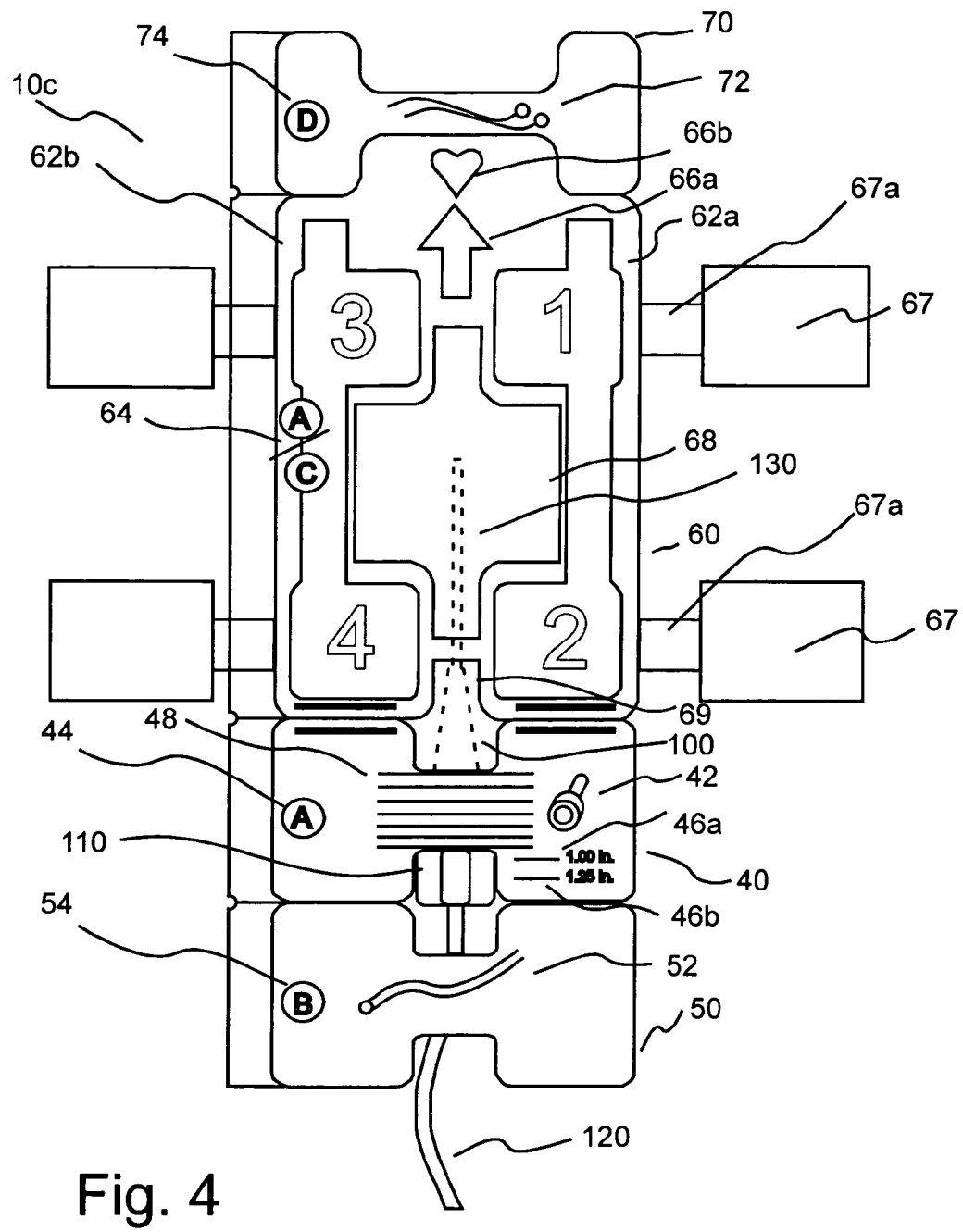
FIG. 4 illustrates a top plan view of another embodiment of an applicator or attachment device of the present invention.

FIG. 4 illustrates a device 10*c* including most of the same components of device 10, and such like components are numbered the same as in FIGS. 1A through 1C. In the embodiment of FIG. 4, device 10*c* includes attachment elements 67 (connected to device 10*c* via flexible arms 67*a*) that attach to the top of antennae 310*a*, 310*b*, 330*a* and 330*b* (for example, via an adhesive) to maintain sensor 300 in operative connection with attachment device 10*c*.

Figure 5:
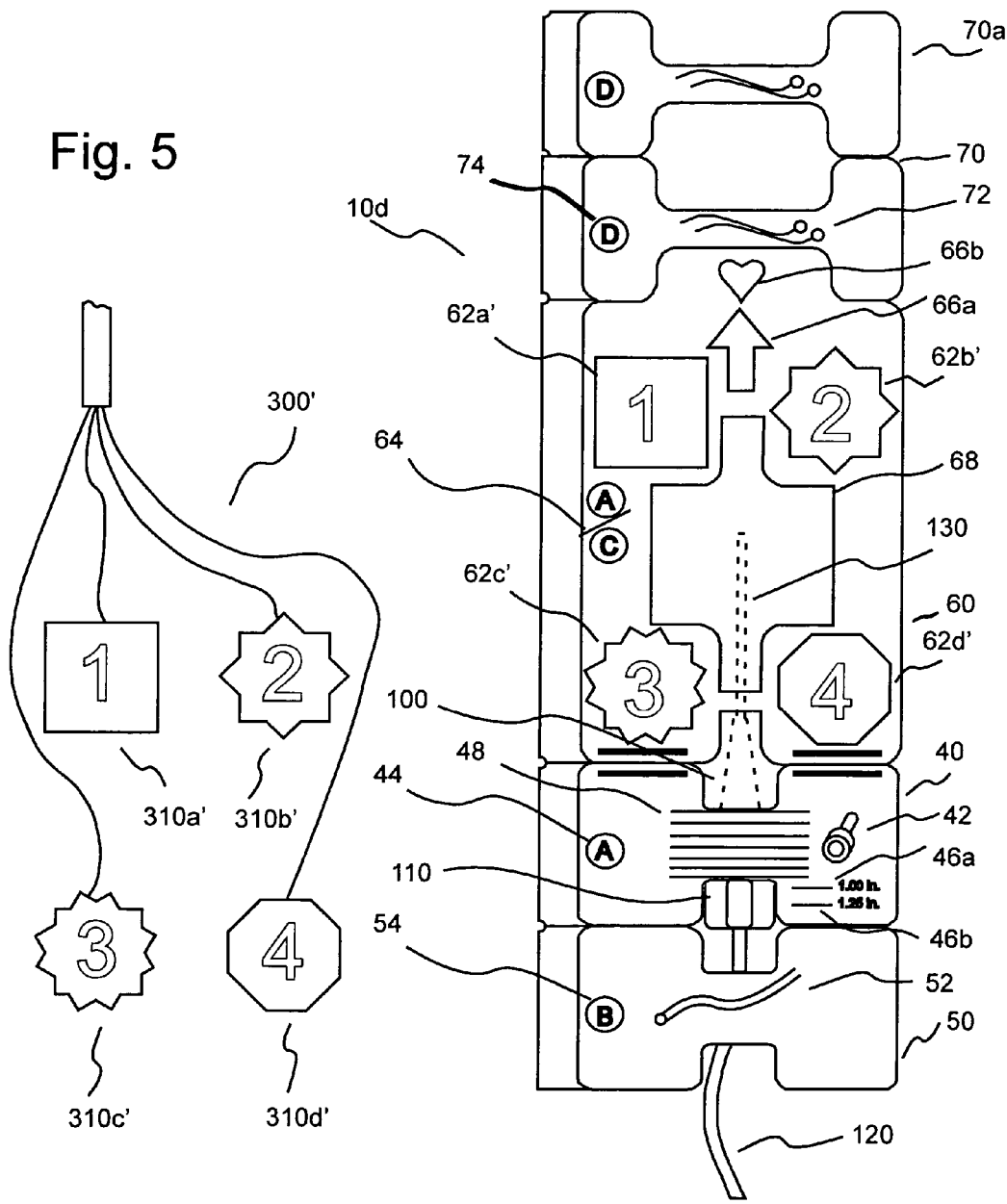
FIG. 5 illustrates a top plan view of another embodiment of an applicator or attachment device of the present invention.

FIG. 5 illustrate a device 10*d* including most of the same components of device 10, and such like components are numbered the same as in FIGS. 1A through 1C. In the embodiment of FIG. 5, device 10*d* includes guide/attachment elements 62*a*', 62*b*', 62*c*' and 62*d*' that are uniquely shaped (and marked with unique indicators—numbers in the embodiment of FIG. 5) to correspond with uniquely shaped (and numbered) antennae 310*a*', 310*b*', 310*c*' and 310*d*' of sensor 300' to ensure proper relative spacing, orientation and positioning of antennae 310*a*', 310*b*', 310*c*' and 310*d*'. Guide elements 62*a*', 62*b*', 62*c*' and 62*d*' can include an adhesive and/or a mechanical attachment element or elements as described above to maintain antennae 310*a*', 310*b*', 310*c*' and 310*d*' in operative connection with attachment device 10*d*.

Figure 6:
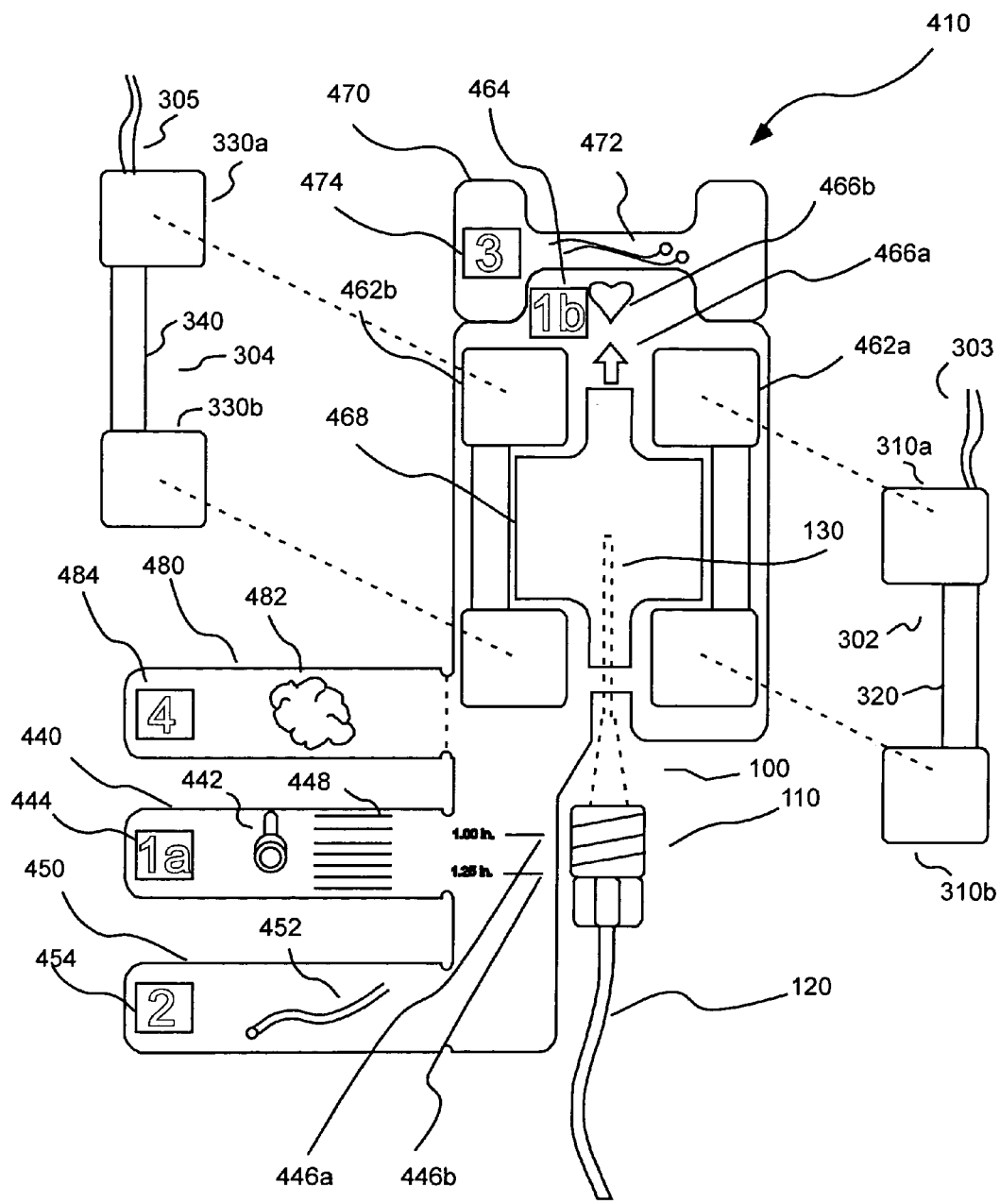
FIG. 6 illustrates a top plan view of another embodiment of a sensor system of the present invention including a sensor and an applicator or attachment device for use in removably attaching the sensor to a patient, wherein the sensor is not attached to the attachment device.

FIG. 6 illustrates another embodiment of a sensor attachment device 410 including many components that operate in a same manner to corresponding components of device 10 of FIGS. 1A through 1C, and such like components are numbered similarly to corresponding components of device 10 with the addition of 400 thereto. In the embodiment of FIG. 6, first section 440, second section 450 and third section 460 are not separable. Third section 460 is very similar in operation to third section 60 of device 10. Unlike first section 40 and second section 50 of device 10, first section 440 and second section 450 are folded to the right (in the orientation of FIG. 6) to attach to catheter hub 110 and tubing 120, respectively, without disconnection thereof. Fourth section 470 is removably attached to third section 460 as described above in connection with fourth section 70.

Sensor attachment device 410 further includes a fifth section 480 removably attached thereto that can be used in connection with, for example, a cotton ball to perform the function of a bandage after catheter 100 and the remainder of device 410 are removed from connection with the patient. Fourth section 480 includes an indicator 482 (for example, representative of a cotton ball) to set forth the recommended use thereof. Fourth section 480 also includes an indicator 484 (for example, the numeral "4") to set forth the recommended order of the user thereof.

Figure 7A:
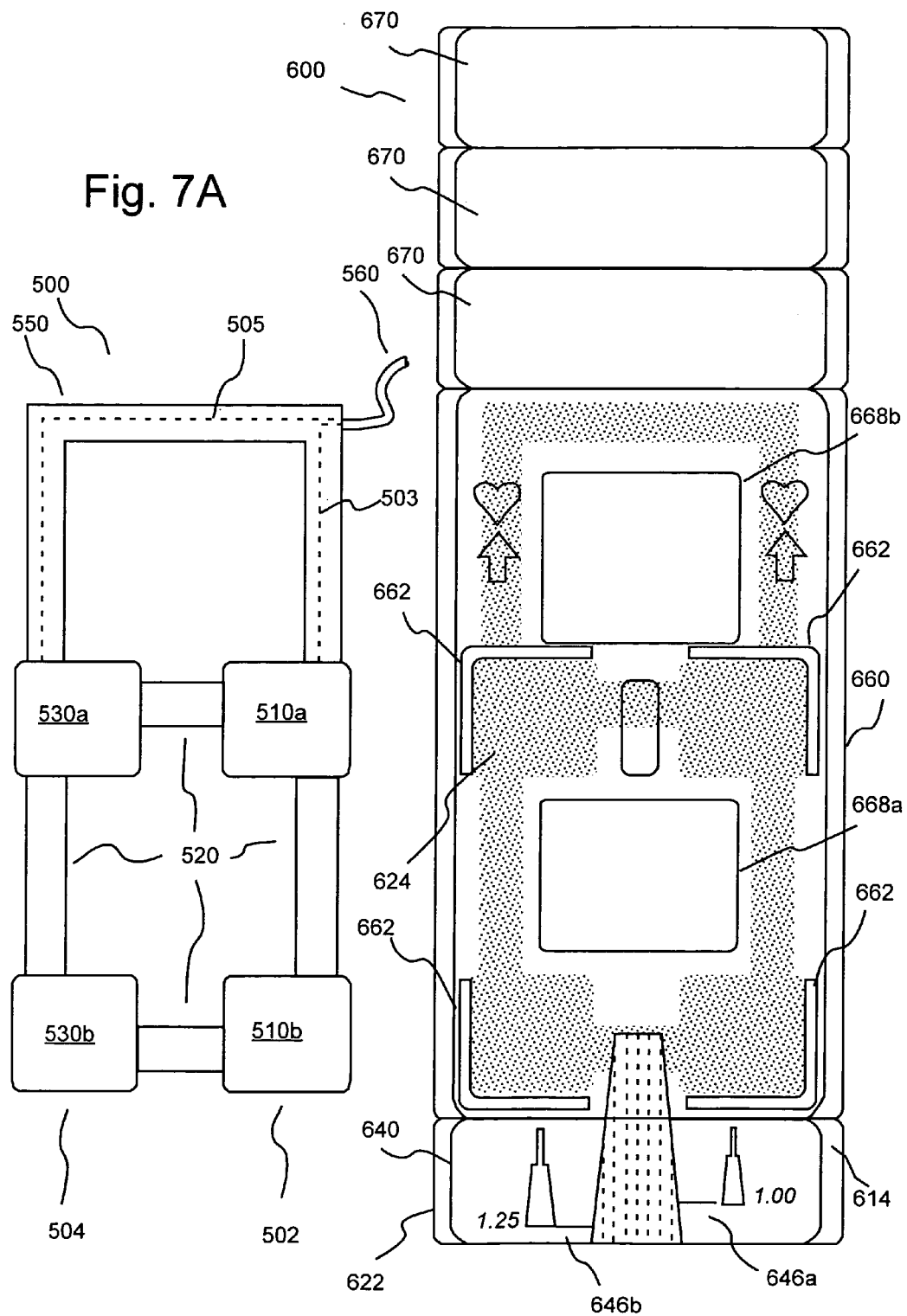
FIG. 7A illustrates a top plan view of another embodiment of a sensor system of the present invention including a sensor and an applicator or attachment device for use in removably attaching the sensor to a patient, wherein the sensor is not attached to the attachment device.
Figure 7B:
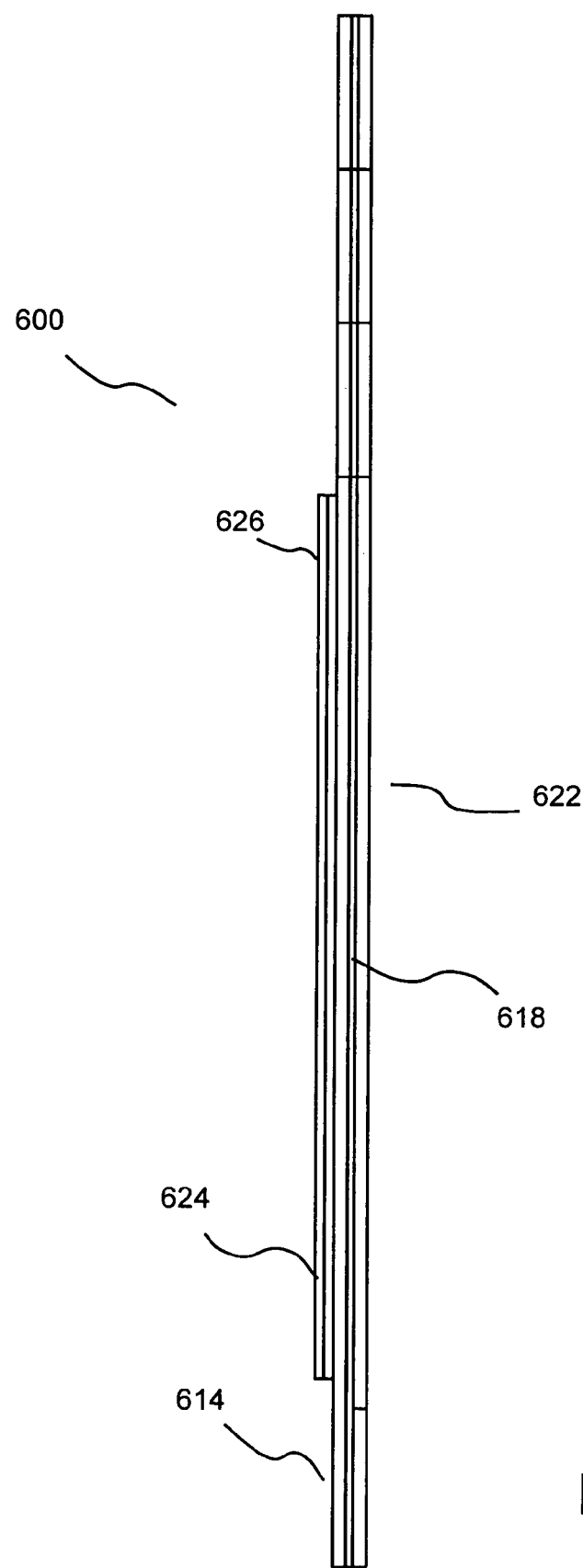
FIG. 7B illustrates a side, cutaway view of the attachment device of FIG. 7A.

FIGS. 7A and 7B illustrate another embodiment of a system of the present invention including an application or attachment device 610 for use with an extravasation sensor 500 which operates in the manner described in Published PCT International Application Nos. WO 03/009753 and WO 03/009752. Extravasation sensor 500 includes a transmitting unit 502 including two transmitting antennae 510*a* and 510*b*. Extravasation sensor 500 further includes a receiving unit 504 including two receiving antennae 530*a* and 530*b*. Antennae 510*a*, 510*b*, 530*a* and 530*b* are interconnected and spaced by bridging members 520. Sensor 500 further includes a cable carrying section 550 which operates to orient and or space cables or wiring 503 and 505 connecting to the sensor antennae. Cable carrying section 550 can, for example, be fabricated from flex cable as used, for example, in the computer and other arts. One or more cabling systems such as coaxial cable systems can be in operative connection with cable carrying section 550 to connect sensor 500 to a control system.

Sensor attachment device 610 includes a base layer 614 similar in purpose and operation to base layer 14 of device 10. An adhesive layer 618 (see FIG. 6B) is applied to a back or rearward major surface of base layer 614. A removable protective or backing layer 622 protects adhesive layer 618 until device 610 or sections thereof is/are placed in use. A first or catheter section 640 operates similarly to first section 40 of device 10 to attach to a catheter hub (not shown in FIGS. 7A and 7B). Indicating elements such as indicators 646*a* and 646*b* can be provided to properly position first section 640 with respect to different length catheters as described above in connection with first section 40 of device 10. A second or sensor section 660 can, for example, remain in connection with first section 640 while first section 640 is applied to the catheter. As described above in connection with device 10, protective layer 622 can be removed from connection with adhesive layer 618 over the area first section 640, while protective layer 622 remains in connection with adhesive layer 618 over the area of second section 660. Protective layer 622 can then be removed from second section 660 for attachment of second section 660 to the patient.

Second section 660 can include guide elements 662 which can, for example, be printed on base layer 614 or comprise upward extending elements to assist in properly aligning antennae 610*a*, 610*b*, 630*a* and 630*b* of sensor 600 with respect to each other and with respect the catheter. In that regard, the end of the catheter needle is preferably generally aligned with a center point of the sensor antennae. Guide elements 662 can also provide a signal that can be sensed by a user (for example, a tactile, a visual, an audible etc. signal) that sensor 600 is positioned and/or connected correctly. Second section 660 can also include an adhesive layer 624 to attach sensor 500 to device 610. A removable cover or protective layer 626 (see FIG. 7B) can be applied to adhesive layer 624 to protective adhesive layer 624 prior to use thereof. Adhesive layer 624 can be applied to base layer 614 so that adhesive does not extend beyond the footprint of sensor 500 to any substantial degree when sensor 500 is attached to device 610. In that regard, adhesive extending beyond the footprint of sensor 600 can lead to a number of problems, including, for example, attracting debris/contaminants and/or sticking to clinician's glove and/other clothing. Mechanical guides such as guide elements 662 and other guides or abutment members can assist in maintaining an adhesive within the footprint of sensor 600.

Second section 660 includes a first open area 668*a* for visualization and/or palpation over the area of the end of the catheter needle. Second section 660 also includes a second open area 668*b* for visualization and/or palpation of an area of the patient further toward the heart of the patient. In that regard, extravasations can occur or are sometimes better detected via palpation and/or visualization "upstream" from the end of the catheter needle. Other open areas can be provided. Moreover, first and second open areas 668*a* and 668*b* can be merged to form a single, larger open area.

Sensor attachment device 610 further includes a plurality of adhesive strip sections 670 that can, for example, be used to attach to sensor cabling, to attach to catheter tubing, and/or to form a bandage in connection with an absorbent materials such as cotton. Adhesive strip sections are removably attached to second section 660 and to each other.

Figure 8A:
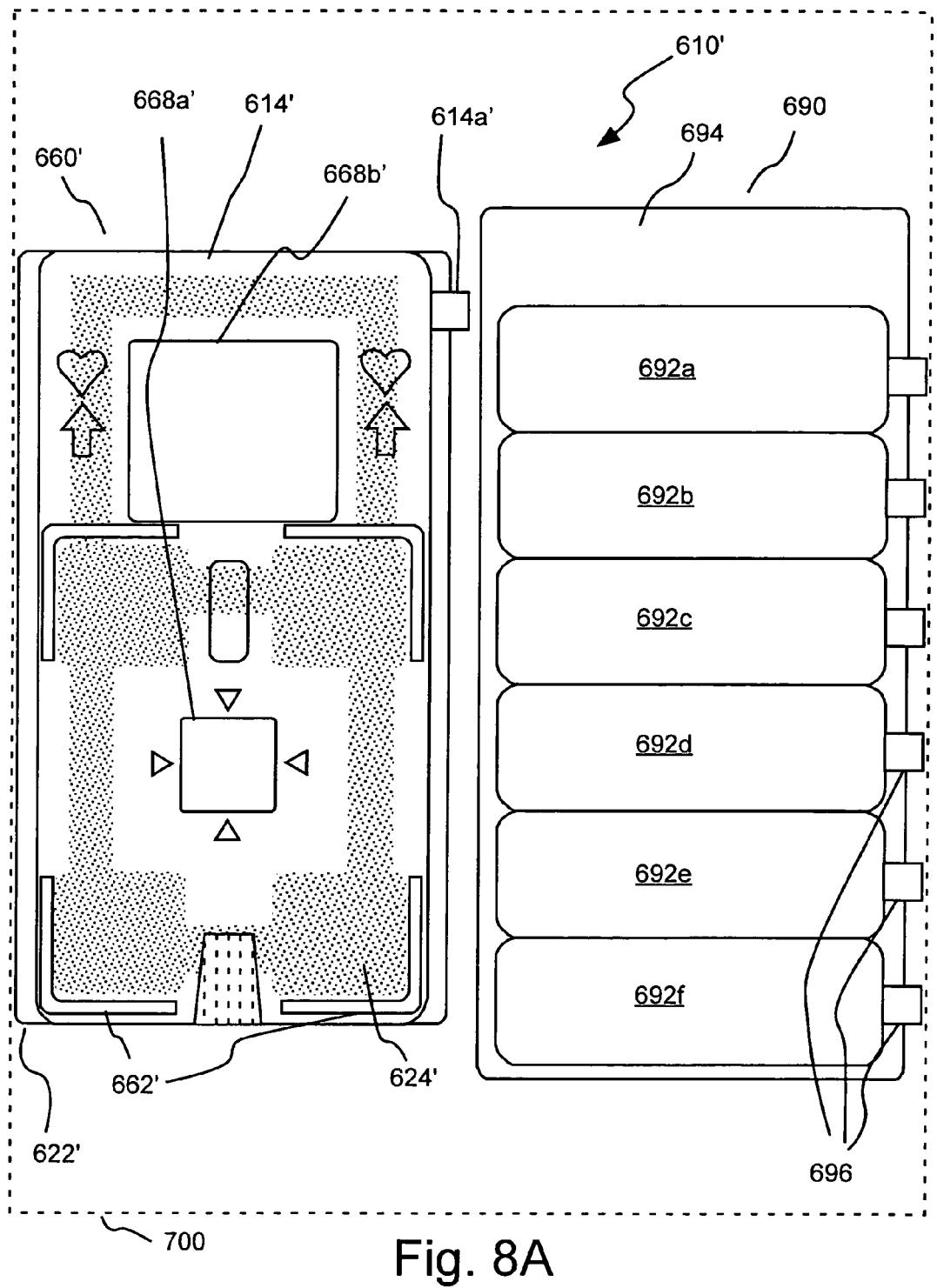
FIG. 8A illustrates a top plan view of another embodiment of an applicator or attachment device of the present invention for use with a sensor and a separate adhesive strip dispensing or supply device.
Figure 8B:
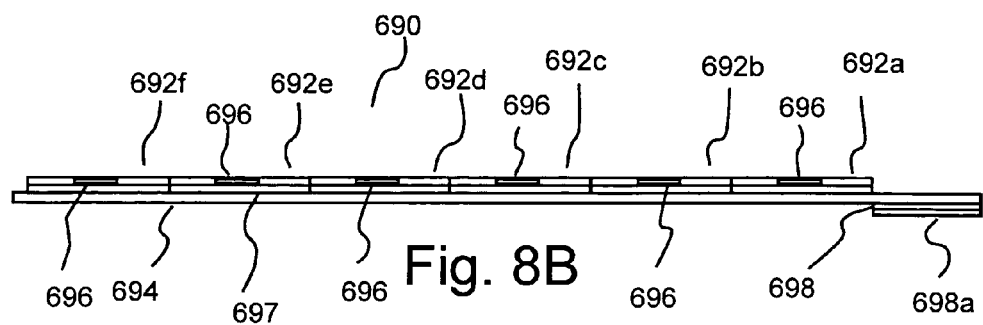
FIG. 8B illustrates a side view of the adhesive strip dispensing or supply device of FIG. 8A.

FIGS. 8A and 8B illustrate an embodiment of an attachment system 610' of the present invention that operates in a number of manners similarly to sensor attachment system 610. In that regard, attachment system 610' includes a sensor attachment section 660', which can include guide elements 662' to assist in properly aligning antennae 510a, 510b, 530a and 530b of sensor 500 with respect to each other and with respect the catheter. Sensor attachment section 660' also includes an adhesive layer 624' on base layer 614' to attach sensor 500 to sensor attachment section 660'. A removable cover or protective layer (not shown) can be applied to adhesive layer 624'.

As discussed above, in certain situations the end of the catheter needle is preferably aligned with the center point of the sensor antennae. Other devices may require other alignment locations. In the embodiment of FIGS. 8A and 8B, attachment system 610' does not include a catheter section such as catheter section 640 of attachment device 610 including alignment indicators to position sensor attachment section 660' with respect to a catheter. Sensor attachment section 660' includes an open area 668a' that is reduced in area as compared to open area 668 of device 610. Operators can typically accurately determine the location of the end of a catheter needle after a catheter has been set in place. In the embodiment of FIGS. 8A and 8B, the operator simply aligns the center of open area 668a' with the end of the catheter needle. Indicia such as arrowheads as illustrated in FIG. 8A can be provided to facilitate alignment. Open area 668a' can, for example, be of a shape other than square or rectangular (such as round or oval) to facilitate proper positioning. Sensor attachment section 660' also includes a second open area 668b' to, for example, visualization and/or palpation.

Base layer 614' can include a tab 614a' that can be used by an operator to remove base layer 614' from connection with protective layer 622'.

Figure 8C:
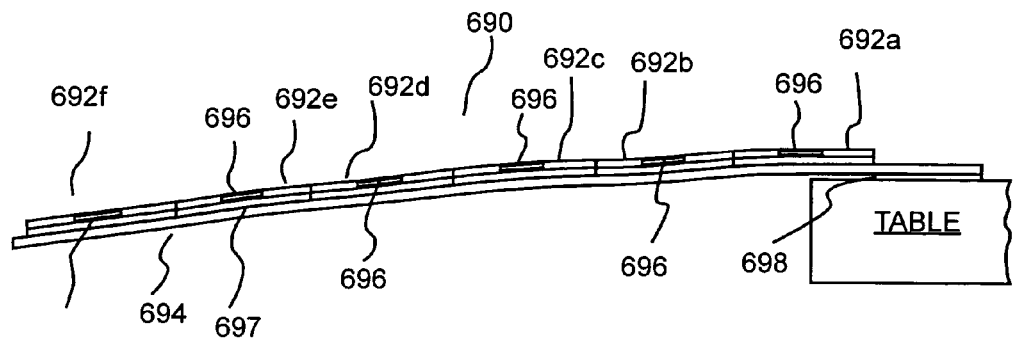
FIG. 8C illustrates a side view of the adhesive strip dispensing or supply device of FIG. 8A removably adhered to a table for ready access thereto.

Sensor attachment system 610' further includes an adhesive strip supply device 690' including a plurality of adhesive strips 692a through 692f which are held upon a base, backing or protective layer 694 via an intermediate adhesive layer 697 (see, for example, FIG. 8B). Adhesive strips 692a through 692f are preferably removable from backing layer 694 using a single hand and can be applied in any number of fashions to, for example, adhere to catheters, tubing, cabling, bandaging etc. In the embodiment of FIGS. 8A through 8C each of adhesive strips 692a through 692f includes a tab 696 that includes no adhesive on a back or rear side thereof. Each tab 696 can be grasped using a single hand to remove one of adhesive strips 692a through 692f.

Figure 9:
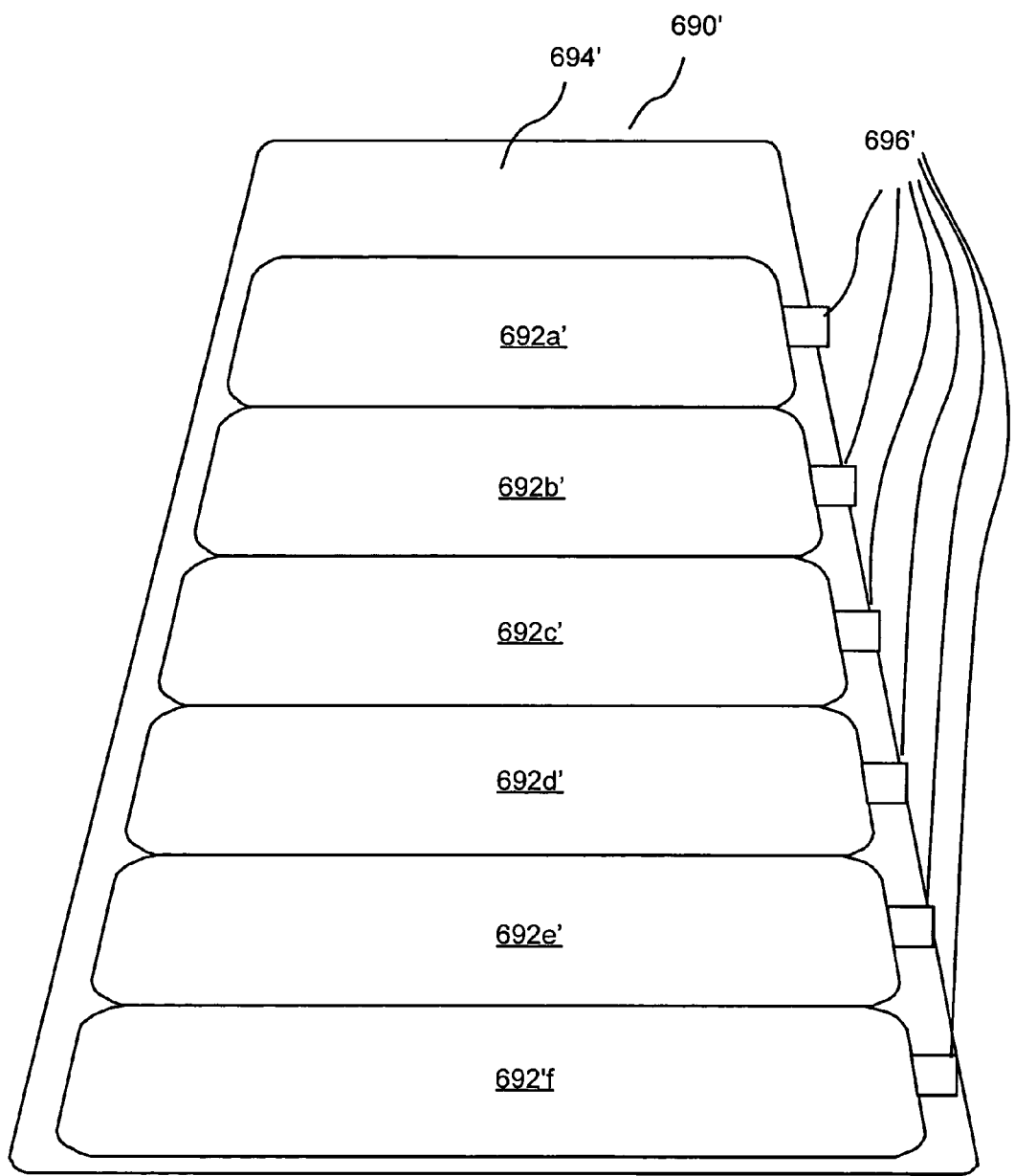
FIG. 9 illustrates a perspective view of the adhesive strip dispensing or supply device similar to that of FIG. 8A, but including adhesive strips of various dimensions.

System 610' or the components thereof (that is, sensor attachment section 660 and adhesive strip supply device 690) can, for example, be sterilizable and can, for example, be supplied or distributed in one or more sterile packages as represented by dashed lines 700 in FIG. 8A. Use of tabs 696 to remove adhesive strips 692a through 692f from backing layer 694 and tab 614a' to remove base layer 614' from backing 622' assists in maintaining sterile or aseptic technique by enabling the user to avoid contact with those portions of adhesive strips 692a through 692f and attachment device 610' which contact a patient. As illustrated in FIG. 9, an adhesive strip supply device 690' can be provided including adhesive strips 692a' through 692f of varied dimensions (for example, length, width etc.)

As illustrated in FIGS. 8B and 8C, at least a portion of a reverse side of backing layer 694 (opposite adhesive layer 697) can be covered with an adhesive layer 698. A cover or protective layer 698a can cover adhesive layer 698 until use thereof. Adhesive layer 698 can, for example, be used to removably attach device 690 to an object such as a table (see FIG. 8C) for convenient access by a user (similar to the manner in with a POST-IT® note as available from 3M of St. Paul, Minn. is attached to an object). Adhesive layer 698 can, for example, have a suitably high peel strength such that each of adhesive strips 692a through 692f can be removed from backing layer 694 with a single hand by grasping one of tabs 696 without the requirement of using the other hand to stabilize device 690. Although adhesive strip supply devices 690 and 690' are well suited for use with the sensor application devices of the present invention, such adhesive strip supply devices can be used in many medical and other procedures. As illustrate in FIG. 8C, backing layer 694 can be relatively stiff to support adhesive strips 692a through 692f and prevent significant bending of backing layer 694 (for example, when attached to a surface).

Figure 10A:
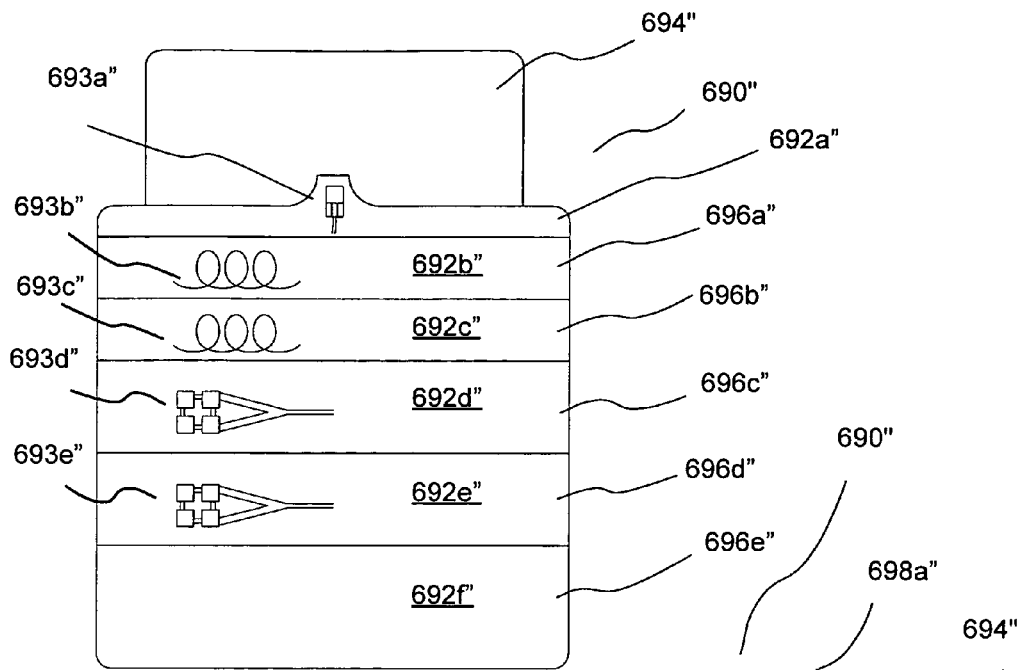
FIG. 10A illustrates a top view of the another embodiment of an adhesive strip dispensing or supply device of the present invention.
Figure 10B:
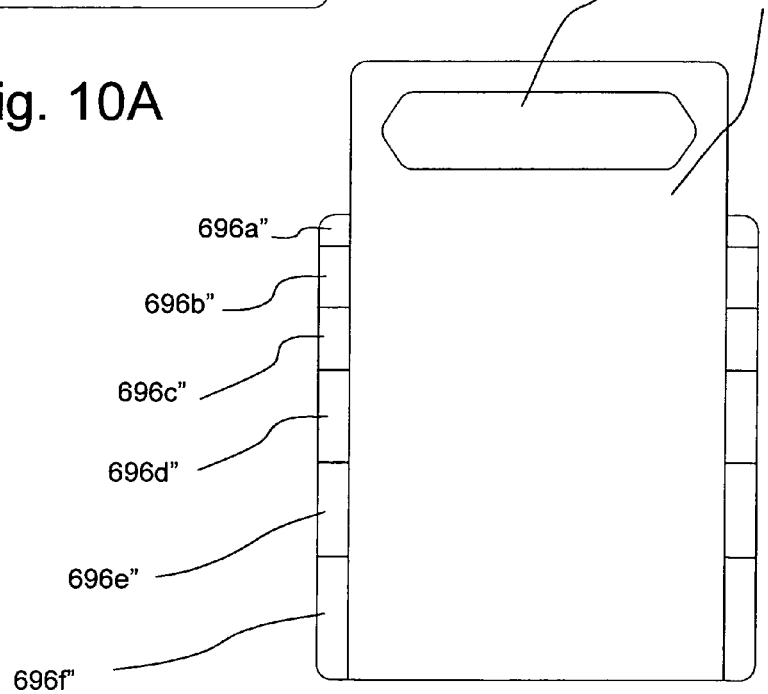
FIG. 10B illustrates a bottom view of the adhesive strip dispensing or supply device of FIG. 10A.

FIGS. 10A and 10B illustrate another embodiment of an adhesive strip supply device 690" including a plurality of adhesive strips 692a" through 692e" which are held upon a backing or protective layer 694" via an intermediate adhesive (not shown, but similar in design and operation to adhesive layer 697 of FIG. 8B). Adhesive strips 692a" through 692e" can be removed from backing layer 694" using a single hand as described above. In that regard, similar to device 690 describe above, device 690" can be attached to a surface using an adhesive layer (not shown, but similar in design and operation to adhesive layer 698 of device 690) on the back or rearward side thereof. As illustrated in FIG. 10B, the rearward adhesive layer can be protected by a cover layer 698a" until use thereof. In the embodiment of FIGS. 10A and 10B, each of adhesive strips 692a through 692f extends beyond the side edges of backing layer 694" to create tab sections 696a" through 696e" which can be grasped by a user to facilitate easy, quick and generally foolproof removal of adhesive strips 692a" through 692e" from backing layer 694". Preferably, the rearward side of tab sections 696a" through 696e" includes no adhesive thereon.

Backing of base layer material 694" is preferably stiffer than the material of adhesive strips 692a" through 692f'. Backing or base layer material 694" is preferably sufficiently stiff to prevent bending of backing or release layer 694" as adhesive strips 692a" through 692f' are removed therefrom. The stiffness of backing layer 694" can be defined by or measured by paper gauge. The gauge of backing layer 694" is preferably at least 50. More preferably, the gauge is at least 75. In several embodiment, paper having a gauge was in the range of approximately 79 to 83 was used for backing layer 694". Moreover, the material(s) for adhesive strips 692a" through 692f' is/are preferably chosen so that that adhesive strips 692a" through 692f' do not curl upon removal from layer 694. The adhesive tape material for adhesive strips 692a" through 692f' preferably has sufficient thickness and tensile modulus to reduce or preclude curling when subjected to the peel force required to remove adhesive strips 692a" through 692f' from the backing or base layer 694". One skilled in the art can readily determine a thickness/weight of material to meet the requirements of various uses. In several embodiments of the present invention the thickness of the material for adhesive strips 692a" through 692f' was in the range of approximately 0.005 to 0.0061 inches. The tensile modulus of the material for adhesive strips 692a" through 692f' was preferably in the range of approximately 80,000 to 120,000 psi. In several embodiment of the present invention, the material for adhesive strips 692a" through 692f' was a flexible polymeric material such as a polyethylene film. The peel strength for the adhesive in several embodiment was preferably in the range of 1400 to 2800 grams/inch. As clear to one skilled in the art, the peel strength can be modified to suit a particular application. The range of peel strength set forth above was found to be suitable for holding cables, catheters and other components for use in connection with various sensor application devices and sensors of the present invention. Moreover, as with the size and shape of the adhesive strips of the adhesive strip supply or dispensing devices of the present invention, the peel strength of the adhesive of the adhesive strips can be varied between adhesive strips in a single such dispensing device to, for example, adapt or "tune" each of the adhesive strips to various suggested uses of such adhesive strips.

As described above, indicia can be provided on the upper surface of the adhesive strips of the present invention to indicate a suggested use of each adhesive strip. For example, in the embodiment illustrated in FIG. 10A, adhesive strip 692*a*" includes an indication 693*a*" suggesting used in connection with a catheter hub. Adhesive strips 692*b*" and 692*c*" include indications 693*b*" and 693*c*", respectively, suggesting use in connection with low pressure tubing (for example, tubing connected to a catheter). Adhesive strips 692*d*" and 692*e*" include indications 693*d*" and 693*e*", respectively, suggesting use in connection with sensor cabling.

In the embodiment of FIGS. 10A and 10B, each of adhesive strips 692*a*" through 692*f* is illustrated to be adjacent to the neighboring adhesive strip without any intervening space. However, space can be provided between the adhesive strips and can, in certain circumstances, facilitate the independent removal of each adhesive strip. The base layers of the adhesive strip dispensing devices of the present invention can, for example, be formed such the adhesive strips are positioned or seated in wells or seatings formed therein.

Figure 11:
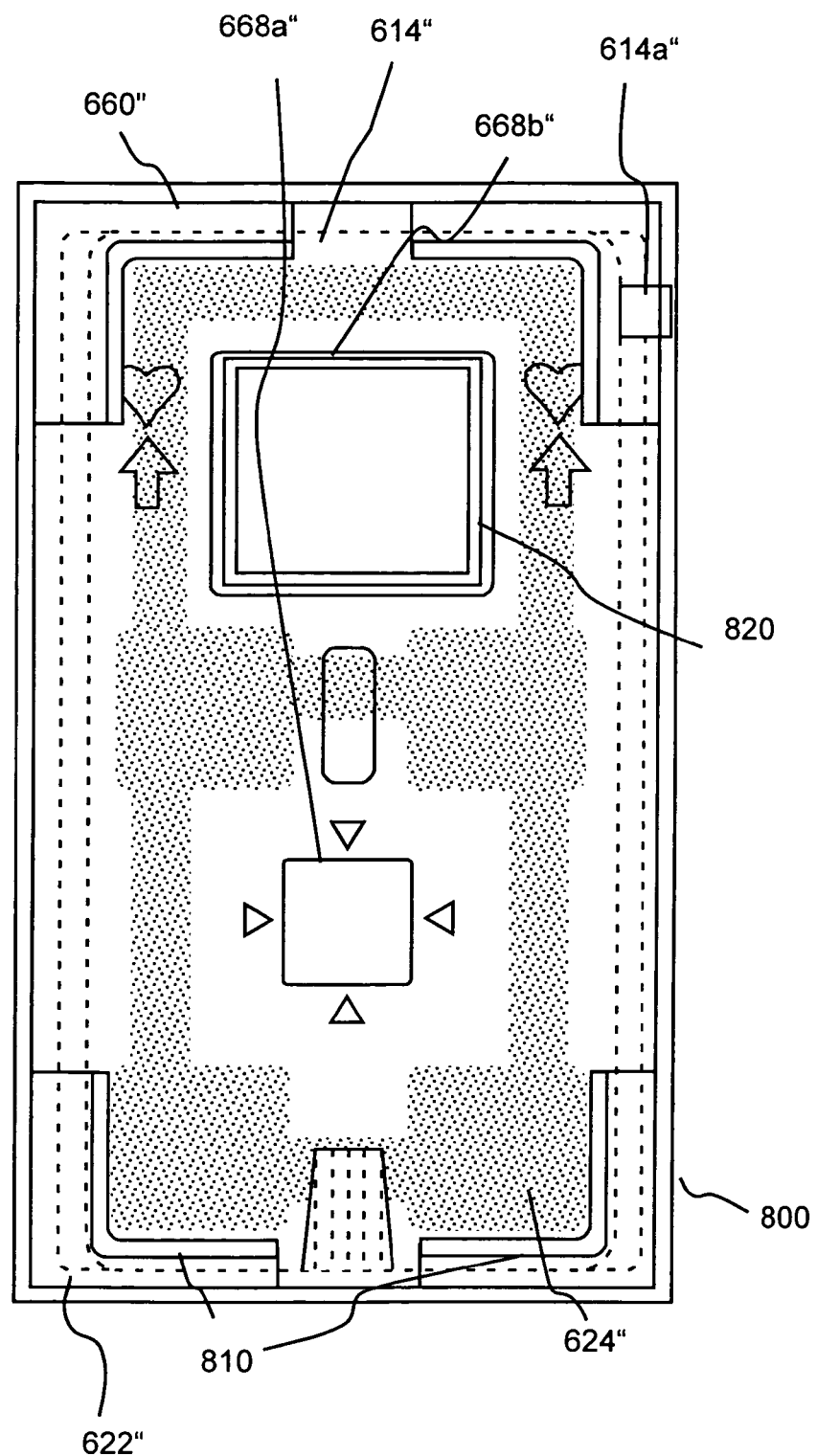
FIG. 11 illustrates an embodiment of a sensor attachment device similar to that of FIG. 8A, wherein the sensor attachment device is positioned within a package or a portion of a packaging system that includes a guide or guides positioning a sensor for attachment of the sensor to the sensor attachment device while the sensor attachment device is still within or partially within the packaging.

FIG. 11 illustrates an embodiment of a sensor attachment device 660" similar in many respects to that of sensor attachment device 660' of FIG. 8A. Like components of device 660" are numbered similarly to corresponding components of device 660'. In the embodiment of FIG. 11, a package 800 or a portion of a packaging system includes guides 810 and 820 to ensure that sensor 500 is attached to device 660" in a proper position and with proper alignment while sensor attachment device 660" is still within or partially within the packaging 800. Guides 810 surround the perimeter of sensor 500, while guide 820 is positioned within cable guide 550 of sensor 500 when sensor 500 is place in contact with attachment device 660". After attachment of sensor 500 to attachment device 660", attachment device 660" (with sensor 500 attached thereto) can be attached to a patient. In the embodiment of FIG. 11, there may be no need for printed or mechanical guides on attachment device 660" to guide the positioning of sensor 500 thereon as that function is performed by packaging 800.

FIGS. 12A through 12F illustrate another embodiment of an attachment system 910 of the present invention that operates in a number of manners similarly to sensor attachment system 610. Attachment system 910 includes a sensor attachment section 960, which can include guide elements 962 (see, FIG. 12F) to assist in properly aligning, for example, antennae 510*a*, 510*b*, 530*a* and 530*b* of sensor 500 with respect to each other and with respect a catheter (not shown). Guide elements 962 can, for example, be printed guides or physical guides as described above. Sensor attachment section 960 also includes an upper adhesive layer or sensor adhesive layer 924 on base layer 914 (see FIG. 12E) to attach a sensor such as sensor 500 to sensor attachment section 960. Sensor adhesive layer 924 can cover the entire surface of sensor attachment section 960, generally only those areas of sensor attachment section that are contacted by the sensor, or an intermediate area of the surface of sensor attachment section 960. A transparent, removable cover or protective layer 970 can be applied to adhesive layer 924. Providing a transparent cover layer can enable the user to see orientation indicia on sensor attachment section 960 as described above. Sensor attachment section 960 further includes a rearward, bottom or patient adhesive layer 918 adapted to attach sensor attachment section 960 to a patient. A cover or protective layer 922 is preferably removably attached to patient adhesive layer 918.

As discussed above, in certain situations the end of the catheter needle is preferably aligned with the center point of the sensor antennae. Other devices may require other alignment locations. In the embodiment of FIGS. 12A through 12F, sensor attachment section 960 includes an open area 968*a* (similar, to open area 668*a*'). In general, operators can determine the location of the end of a catheter needle after a catheter has been set in place. The operator simply aligns the center of open area 968*a* with the end of the catheter needle. Indicia 968*a*' (arrows in the embodiment of FIG. 12F) can be provided to facilitate the alignment. Visualization and/or palpation of the area of the catheter needle tip can be achieved through open area 968. A second open area 968*b* for visualization and/or palpation can also be provided. Through second open area 968*b*, an operator can also, for example, feel the flow of fluid through the blood vessel (sometimes referred to as the "thrill"), which can provide feedback of proper catheter insertion and operation. One or both of open areas 968*a* and 968*b* can be provided with transparent cover layer 969*a* and 969*b*, respectively, (for example, a relatively thin polymeric film) which can assist in maintaining sterility. Preferably, transparent covers 969*a* and 969*b* are sufficiently transparent and sufficiently flexible so that they do not interfere to any substantial degree with visualization and/or palpation. Covering openings or palpation/visualization windows 968*a* and 969*b* with, for example, a thin transparent membrane 969*a* and 969*b*, respectively, can assist in preventing contamination of the "cleansed" area of the IV site even if an operator palpates the site through the membrane without sterile gloves or using a non-covered hand.

As described above, in connection with attachment system 610, attachment system 910 can further include alignment guides or indicia 946*a* and 946*b* (see FIG. 12F) to assist in proper positioning of sensor attachment system 910 with respect to one or more standard catheter sizes. More than one attachment system 910 can be provided to facilitate use with a wide variety of catheter designs and sizes so that a catheter tip is appropriately positioned within opening 968*a* without interference with an attached sensor.

Sensor attachment section 960 further includes a catheter protective section 948 that is connected to the remainder of sensor attachment section 960 in, for example, the manner of a flap at area 949. Catheter protective section 948 can, for example, be die cut. Catheter protective section 948 covers a portion of the catheter to, for example, cover the puncture site and assist in maintaining sterility.

In the embodiment of FIGS. 12A through 12F, attachment system 910 also includes a removal tab section 980 to facilitate removal of sensor attachment section 960 from attachment to a patient after a procedure. Removal tab section 980 can, for example, be attached to sensor attachment section 960 via adhesive layer 924. After a procedure, a user can simply grasp the end of removal tab section 980 an apply an upward force to remove sensor attachment section 960 from the patient.

In several embodiments of the sensor attachment devices of the present invention, the various layers of such sensor attachment devices were fabricated from a flexible polymeric material such as a polyester film material.

As described above, the attachment devices, systems and methods of the present invention can be used in attaching many medical devices to patient or to other articles. The attachment devices of the present invention, which can be provided in sterile condition can assist in preventing contaminants from passing from a reusable medical device to a patient. Likewise, the attachment devices of the present invention can prevent contaminants from passing from a patient to a reusable medical device.

The attachment devices, systems and methods of the present invention are particularly useful in attaching sensors such as disclosed in Published PCT International Application Nos. WO 03/009753 and WO 03/009752 to patients. In that regard, the sensor attachment devices, systems and methods of the present invention enable the ready attachment of such sensors and other medical devices to a patient and proper alignment thereof with respect to a volume of interest (for example, a volume surrounding or in the vicinity of the tip of a catheter needle). The attachment, devices, systems and methods of the present invention provide for secure, removable connection of the sensor or other medical device to the patient without the occurrence of wrinkles and/or air pockets that can result in artifacts or improper measurements by the sensor.

Moreover, the sensor can be readily removed from the attachment devices of the present invention for reuse. The attachment devices are removable from contact with the patient and are disposable after a single use. U.S. Provisional Patent Application No. 60/553,374 discloses removable adhesive systems for sensor attachment and other devices that can be used in connection with the present invention to facilitate removal of the attachment devices of the present invention from connection with the patient.

The adhesive layer or layers of the devices of the present invention which contact the patient can include one or more materials that can, for example, be biologically active (bioactive agents) or otherwise active, for example, to cause, to enhance, to accelerate, to decelerate, to inhibit or to prevent some action. In general, bioactive agent affect at least one of biological activity or chemical activity in an organism. Bioactive agents may be synthetic molecules, biomolecules or multimolecular agents and include, but are not limited to, enzymes, organic catalysts, ribozymes, organometallics, proteins, glycoproteins, peptides, polyamino acids, antibodies, nucleic acids, steroidal molecules, anesthetics, antibiotics, antivirals, analgesics, antimycotics, anticancer agents, anti-rejection agents, anticlotting agents, immunosuppressants, cytokines, carbohydrates (for example, saccharides, polysaccharide, starch etc.), oleophobics, lipids, and various other pharmaceuticals, chemotherapeutics and therapeutics.

Although the present invention has been described in detail in connection with the above embodiments and/or example, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:
1. A system for detection of extravasation, comprising:
 a sensor comprising:
  at least one transmitting antenna to apply electromagnetic energy in the frequency range of approximately 300 MHz to approximately 30 GHz to a volume of the body over a period of time;
  at least one receiving antenna to measure a resultant signal;
 a device for attaching the sensor to a patient, comprising:
  a base layer;
  an adhesive layer on a rearward side of the base layer, the adhesive layer being adapted to removably attach the base layer;
  a sensor attachment mechanism on a forward side of the base layer, the sensor attachment mechanism being adapted to removably attach the sensor to the base layer;
  a cable lead section disposed proximal to the sensor attachment mechanism;
  a direction indicator disposed on the sensor attachment mechanism;
 a catheter attachment section disposed distally from the sensor attachment mechanism; and
  a tubing section disposed distally from the catheter attachment mechanism and
  a device for dispensing adhesive strips, comprising:
  a backing layer; and
  a plurality of adhesive strips removably adhered to a forward side of the backing layer, each of the adhesive strips including a dispensing base layer and a dispensing adhesive layer on the rearward side of the base layer, the dispensing adhesive layer removably adhering the adhesive strip to the dispensing backing layer, at least a portion of the dispensing adhesive layer remaining in contact with the dispensing base layer after removal of the adhesive strip from the dispensing backing layer.

2. The system of claim 1 wherein the sensor attachment mechanism comprises at least one adhesive layer on the base layer.

3. The system of claim 2 wherein the at least one adhesive layer is positioned on the base layer so that it does not extend beyond a footprint of the sensor when the sensor is attached to the base layer.

4. The system of claim 1 wherein the base layer of the sensor attachment device comprises at least one open area to enable at least one of palpation or visualization of an area of the patient.

5. The system of claim 1 wherein the sensor attachment device further comprises at least one application guide to position the sensor attachment device at a desired position on the patient.

6. The system of claim 5 wherein the sensor attachment device further includes at least one sensor guide to position the sensor at a desired position on the sensor attachment device.

7. The system of claim 5 wherein the application guide assists in positioning the sensor attachment device relative to a catheter.

8. The system of claim 7 wherein the application guide comprises an indicator on the base layer of the device.

9. The system of claim 1 wherein the sensor attachment device further comprises at least one adhesive strip removably attached to the base layer, the adhesive strip having an adhesive on a rearward side thereof.

10. The system of claim 9 wherein the adhesive strip includes an indicator thereof representative of a proposed use thereof.

11. The system of claim 1 wherein the sensor attachment device further comprises a plurality of adhesive strips removably attached to the base layer, each of the adhesive strips having an adhesive on a rearward side thereof.

12. The system of claim 1 wherein the sensor attachment device further comprises a section adapted to cover at least an area in which a catheter enters the patient when the device is attached to a patient.

13. The device of claim 4 wherein the sensor attachment device further comprises a transparent, flexible material covering the open area.

14. The device of claim 1 wherein the base layer of the sensor attachment device comprises at least a first open area and a second open area to enable at least one of palpation or visualization of the patient, the sensor attachment device further comprising a first transparent, flexible material covering the first open area and a second transparent, flexible material covering the second open area.

15. The system of claim 1 wherein the dispensing device is fabricated from sterilizable materials.

16. The system of claim 15 wherein each of the plurality of adhesive strips includes a tab connected to the dispensing base layer that can be grasped by a user to remove each of the adhesive strips from the dispensing backing layer.

17. The system of claim 1 further comprising a layer of adhesive over at least a portion of a rearward side of the dispensing backing layer to enable removable attachment of the dispensing device to an article to enable ready access to the plurality of adhesive strips.

18. The system of claim 1 wherein the dispensing base layer of the device for attaching the sensor is suitable to reduce passage of contaminants between patient and the medical device.

19. The system of claim 1 wherein the adhesive layer on a rearward side of the dispensing base layer of the device for attaching the sensor to a patient comprises a bioactive agent.

20. The system of claim 1 wherein the adhesive layer on a rearward side of the dispensing base layer of at least one of the adhesive strips comprises a bioactive agent.

21. The system of claim 1 wherein the dispensing base layer of the device for attaching the sensor to a patient is divided into a plurality of base layer sections.

22. The system of claim 1 wherein the interactive guide provides at least one of order attachment and proper positioning.

23. The system of claim 1 wherein the medical related delivery devices include catheter or needle.

24. The system of claim 1 wherein the monitoring devices include sensor or cable leads.

* * * * *

UNITED STATES PATENT AND TRADEMARK OFFICE
CERTIFICATE OF CORRECTION

PATENT NO. : 8,235,949 B2
APPLICATION NO. : 11/223792
DATED : August 7, 2012
INVENTOR(S) : Hack et al.

It is certified that error appears in the above-identified patent and that said Letters Patent is hereby corrected as shown below:

ON THE TITLE PAGE

In Item (57), under "ABSTRACT", delete "layer," and insert -- layer. --, therefor.

IN THE DRAWINGS

In Fig. 9, Sheet 11 of 14, delete "692'f" and insert -- 692f --, therefor.

IN THE SPECIFICATION

In Column 3, Line 21, delete "layer," and insert -- layer. --, therefor.

In Column 3, Line 51, delete "in an" and insert -- in a --, therefor.

In Column 5, Line 36, delete "A" and insert -- An --, therefor.

In Column 7, Line 20, delete "such a" and insert -- such as --, therefor.

In Column 8, Line 2, delete "attached" and insert -- attach --, therefor.

In Column 10, Line 7, delete "includes" and insert -- include --, therefor.

In Column 10, Line 7, delete "as an" and insert -- as a --, therefor.

In Column 10, Line 34, delete "avoided," and insert -- avoided. --, therefor.

In Column 15, Line 1, delete "embodiment" and insert -- embodiments --, therefor.

In Column 16, Line 65, delete "an apply an" and insert -- and apply an --, therefor.

In Column 17, Line 56, delete "example," and insert -- examples, --, therefor.

Signed and Sealed this
Twenty-fifth Day of June, 2013

Teresa Stanek Rea
*Acting Director of the United States Patent and Trademark Office*

CERTIFICATE OF CORRECTION (continued)
U.S. Pat. No. 8,235,949 B2

IN THE CLAIMS

In Claim 1, Column 18, Line 3, delete "of the body", and insert -- of a body --, therefor.

In Claim 1, Column 18, Line 6, delete "a device for attaching", and insert -- a sensor attachment device for attaching --, therefor.

In Claim 1, Column 18, Line 21, delete "mechanism and" and insert -- mechanism; and --, therefor.

In Claim 1, Column 18, Line 22, delete "a device for dispensing adhesive strips, comprising:", and insert -- a dispensing device for dispensing adhesive strips, the dispensing device comprising: --, therefor.

In Claim 1, Column 18, Line 27, delete "adhesive layer on the rearward side of the base layer,", and insert -- adhesive layer on a rearward side of the dispensing base layer, --, therefor.

In Claim 1, Column 18, Lines 28-29, delete "removably adhering the adhesive strip to the dispensing backing layer," and insert -- removably adhering each of the adhesive strips to the backing layer, --, therefor.

In Claim 7, Column 18, Line 52, delete "the application guide" and insert -- the at least one application guide --, therefor.

In Claim 8, Column 18, Line 55, delete "the application guide" and insert -- the at least one application guide --, therefor.

In Claim 10, Column 18, Lines 61-62, delete "wherein the adhesive strip includes an indicator" and insert -- wherein the adhesive strip of the sensor attachment device includes an indicator --, therefor.

In Claim 13, Column 19, Line 5, delete "device" and insert -- system --, therefor.

In Claim 13, Column 19, Lines 6-7, delete "material covering the open area", and insert -- material covering the at least one open area --, therefor.

In Claim 14, Column 19, Line 8, delete "device" and insert -- system --, therefor.

In Claim 16, Column 19, Line 18, delete "adhesive strips include a tab", and insert -- adhesive strips of the dispensing device include a tab --, therefor.

In Claim 18, Column 20, Lines 4-5, delete "layer of the device for attaching the sensor is suitable to reduce passage of contaminants between patient", and insert -- layer of the sensor attachment device is suitable to reduce passage of contaminants between the patient --, therefor.

In Claim 19, Column 20, Lines 7-9, delete "adhesive layer on a rearward side of the dispensing base layer of the device for attaching the sensor to a patient comprises", and insert -- adhesive layer on the rearward side of the dispensing base layer of the sensor attachment device to the patient comprises --, therefor.

In Claim 20, Column 20, Lines 10-11, delete "on a rearward", and insert -- on the rearward --, therefor.

CERTIFICATE OF CORRECTION (continued)
U.S. Pat. No. 8,235,949 B2

IN THE CLAIMS

In Claim 21, Column 20, Line 14, delete "of the device for attaching the sensor to a patient", and insert -- of the sensor attachment device to the patient --, therefor.

In Claim 22, Column 20, Lines 16-17, delete "claim 1 wherein the interactive guide provides", and insert -- claim 1 further comprising an interactive guide that provides --, therefor.

In Claim 23, Column 20, Lines 19-20, delete "claim 1 wherein the medical related delivery devices include catheter or needle.", and insert -- claim 1 further comprising a medical related delivery device selected from at least one of a catheter or a needle. --, therefor.

In Claim 24, Column 20, Lines 21-22, delete "claim 1 wherein the monitoring devices include sensor", and insert -- claim 1 further comprising monitoring devices that include a sensor --, therefor.